United States Patent [19]
Dennis

[11] Patent Number: 5,512,456
[45] Date of Patent: Apr. 30, 1996

[54] METHOD FOR THE IMPROVED PRODUCTION AND RECOVERY OF POLY-β-HYDROXYBUTYRATE FROM TRANSFORMED *ESCHERICHIA COLI*

[75] Inventor: Douglas E. Dennis, Weyers Cave, Va.

[73] Assignee: James Madison University, Harrisonburg, Va.

[21] Appl. No.: 890,925

[22] Filed: May 29, 1992

Related U.S. Application Data

[63] Continuation-in-part of Ser. No. 705,806, May 24, 1991, abandoned, which is a continuation-in-part of Ser. No. 528,549, May 25, 1990, abandoned.

[51] Int. Cl.⁶ .............................. C12P 21/06; C12P 7/52; C12P 1/04
[52] U.S. Cl. ..................... 435/69.1; 435/141; 435/170
[58] Field of Search ................ 435/141, 252.33, 435/146, 69.1

[56] References Cited

PUBLICATIONS

Slater et al., "Cloning and Expression in *E. coli* of the *A. eutrophus* H16 PHB Biosynth. Pathway", J. Bact. 170(10):4431–4436 (Oct. 1988).

Studier et al., "Use of T7 RNA Polymerase to Direct Expression of Cloned Genes", Meth. Enz. 185:60–89 (1990).

*Primary Examiner*—Stephanie W. Zitomer
*Attorney, Agent, or Firm*—Seed and Berry

[57] ABSTRACT

Poly-β-hydroxybutyrate is produced by providing a culture of *Escherichia coli* bacterial host cells transformed by a DNA sequence coding for the biosynthetic pathway of poly-β-hydroxybutyrate and a DNA sequence coding for the lysozyme gene; growing the culture and obtaining expression of the poly-β-hydroxybutyrate biosynthetic pathway and the lysozyme gene in each *Escherichia coli* bacterial host cell; lysing the *Escherichia coli* bacterial host cells and collecting the poly-β-hydroxybutyrate. An *Escherichia coli* HMS174(p4A [BstB], pLysS) deposited with the American Type Culture Collection under Accession No. 69001, comprising a plasmid containing a biosynthetic pathway coding for poly-β-hydroxybutyrate and a plasmid containing a lysozyme gene is disclosed.

20 Claims, 24 Drawing Sheets

METHOD FOR THE IMPROVED PRODUCTION AND RECOVERY OF POLY-β-HYDROXYBUTYRATE FROM TRANSFORMED *ESCHERICHIA COLI*

This is a continuation-in-part of U.S. Ser. No. 07/705,806, filed May 24, 1991 which is a continuation-in-part of U.S. Ser. No. 528,549, filed May 25, 1990, both of which are expressly incorporated herein by reference, both now abandoned.

TECHNICAL FIELD

The present invention is generally related to the production of poly-beta-hydroxybutyrate (PHB) using *Escherichia coli* (*E. coli*) which has been genetically transformed by a vector carrying the genes coding for the PHB biosynthetic pathway and, more particularly, to the more efficient production and recovery of PHB from transformed *E. coli*.

BACKGROUND ART

PHB is an energy storage material produced by a variety of bacteria in response to environmental stress and is a homopolymer of D-(−)-3-hydroxybutyrate which has properties comparable to polypropylene, Although poly-β-hydroxybutyrate was first described over 60 years ago, the technological potential of the polymer and related polymers is only now being realized. There is increasing pressure to produce biodegradable plastics due to the problems of waste disposal in general, and disposal of long-lived plastics, specifically. Because PHB is biodegradable, there is considerable interest in using PHB for packaging purposes as opposed to other plastic materials in order to reduce the environmental impact of garbage. PHB also has utility in antibiotics, drug delivery, medical suture and bone replacement applications.

Despite PHB's advantages over other materials, its high cost of production has hindered its performance in the market. The production of the PHB polymer requires extensive treatment after the fermentation phase in order to purify the PHB. This treatment includes mechanical lysis, enzymatic treatment, detergent treatment, washing, agglomeration, and spray-drying. These procedures are expensive and also tend to break down the released granule of PHB.

Currently, two industrial entities are producing PHB. However, the costs of production and recovery of PHB are too high to ensure the use of the plastic as a commodity item. In the first case a regimen of enzymatic treatment and mechanical disruption is used to release the PHB granules from the cells, whereas in the second case, a chlorinated hydrocarbon is used to extract the PHB. In addition, "to the commercial methods currently employed" the related granules can be separated from cell debris by aggregation with salts, such as calcium chloride and other hardening agents, as described in the copending application Ser. No. 07/528,549, filed May 25, 1990.

In a copending patent application Ser. No. 07/362,514 filed Jun. 7, 1989, and in Slater et al., "Cloning and Expression in *Escherichia coli* of the *Alcaligenes eutrophus* H16 Poly-β-Hydroxybutyrate Biosynthetic Pathway", *J. Bact.*, 170:4431, (October 1988), *E. coli* was genetically transformed with genes from *A. eutrophus* which code for the PHB biosynthetic pathway. The cloning of the PHB pathway and its expression in *E. coli* were also later discussed in Schubert et al., *J. Bact.* 170:5837 (December 1988), Peoples et al., *J. Biol. Chem.* 264:15293 (1989a) and Peoples et al., *J. Biol. Chem.* 264:15298 (1989b). These patent applications and references and all references cited in this disclosure are expressly incorporated herein by reference.

Initial experiments indicated that PHB production in transformed *E. coli* has not been greater than about 50%, i.e., 30% (Schubert et al., supra.), 50% (Peoples et al., 1989b), 30–54% (Slater et al., supra.) of the bacterial cell weight. However, in a copending patent application to Dennis et al., Ser. No. 07/768,008, filed Sep. 27, 1991, improvements have been made to the transformed *E. coli* PHB production system that result in levels of intracellular PHB as high as 95% of the cell dry weight. PHB accumulation at this level results in a productivity in *E. coli* (grams produced per liter of culture per hour of time) which is significantly higher than the PHB productivity in *A. eutrophus*.

There is a need to develop a procedure wherein the PHB granules are gently and efficiently released from the *E. coli* cell. There is a further need to develop a PHB recovery system which is superior to the existing technology. The result of procedure would be more efficient production of PHB biodegradable plastic products at a greatly reduced cost.

It is therefore an object to the present invention to provide an improved method for producing PHB in transformed *E. coli*.

It is another object of this invention to provide an improved method for accumulating and recovering PHB from *E. coli*.

It is another object of this invention to provide transformed *E. coli* strains which produce high levels of PHB and which can be readily lysed to release such PHB.

DISCLOSURE OF INVENTION

According to the present invention, PHB can be produced at levels of about 90–95% of the cell weight through the use of (1) a gene dosage effect of a plasmid bearing the PHB biosynthetic pathway (such as the p4A plasmid) and/or (2) a "runaway replication" vector containing the PHB biosynthetic pathway. Both types of plasmid vectors accomplish high PHB production by increasing the number of copies of PHB biosynthetic genes in the cell to approximately 500–1000 copies per cell when the cells are grown in Luria broth.

According to the present invention the PHB biosynthetic pathway can be inserted into a runaway replication vector, which is then transferred into a bacterial host such as *E. coli*. In experiments where the plasmid copy number is increased by heat induction, PHB levels of about 85% to about 90% of the cell weight have been obtained when the construct is grown on Luria broth plus glucose.

Further, according to the present invention, the host bacterial cells are effectively lysed without the need for mechanical action or the addition of enzymatic materials. This is particularly important for the gentle release of PHB granules from the cells. A plasmid containing a lysozyme gene is placed into a bacterial host cell which contains a plasmid bearing the PHB biosynthetic pathway. Thus, the host cells have two plasmids; one plasmid contains the genes for PHB production (optionally a runaway replication vector), and the other plasmid contains the genes for expression of a lysozyme enzyme. The transformed host cell culture is grown for a period of time, during which the PHB granules and the lysozyme enzyme accumulate in the cell. The inner membrane of the host cell does not allow the lysozyme to diffuse through to the peptidoglyan structural or middle layer. At the end of the growth period the inner membrane of the host cell is permeabilized by, for example, exposure to a permeabilizing agent such as ethylene diamine tetracetic acid (EDTA). This allows the lysozyme to access and weaken the structural peptidoglycan layer located between the inner and outer membranes. For example, if the host cells are resuspended in a solution that contains a (1) an agent such as a nonionic surfactant; and (2) is low in salt and/or if the cells are subjected to repeated freeze-thaw cycles, the weakened bacterial cell ruptures due to osmotic lysis. The granules of PHB are released from the host cell and recovered, by for example, agglomerating the granules with a suitable agglomerating agent.

BRIEF DESCRIPTION OF THE DRAWINGS

The foregoing and other objects, aspects and advantages will be better understood from the following detailed description of the preferred embodiments of the invention with reference to the drawings, in which.

BEST MODE OF CARRYING OUT INVENTION

The present invention advantageously provides for increased production of poly-β-hydroxybutyrate (PHB) using E. coli which has been genetically transformed by a vector carrying the genes coding for the PHB biosynthetic pathway.

Figure 1:
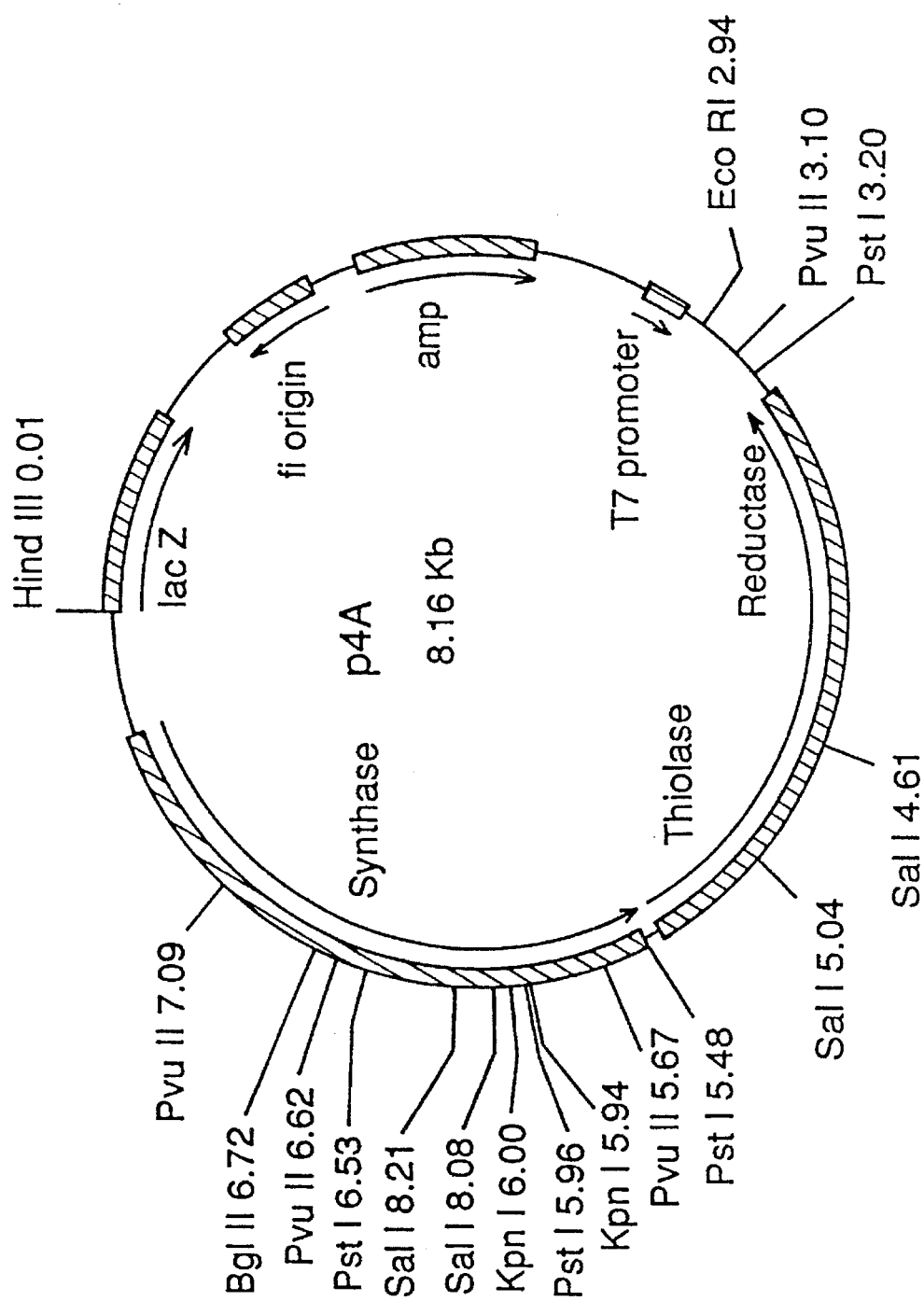
FIG. 1 is a schematic diagram of the plasmid p4A.

The cloning of the PHB pathway and its expression in E. coli was first disclosed and claimed in the copending application Ser. No. 7/362,514 and disclosed in the Slater et al., supra, article. The "first generation" clones consisted of a 5.2 kb KpnI-EcoRI fragment containing the PHB biosynthetic pathway cloned into the vectors pTZ18U-PHB (United States Biochemicals)or pGEM7f+ (Promega Biotec). These clones have approximately 800 bases of non-essential information to the upstream side of the pathway, and 400 bases of non-essential information to the downstream side. In various experiments, these clones produced PHB to levels reaching approximately 50% of the total cell weight. A specific clone that outperforms these clones by a considerable margin is shown in FIG. 1. This clone, designated p4A, is a derivative of pTZ18U-PHB in which approximately 400 bases of the insert DNA (PHB genes) have been deleted starting at the unique HindIII site. The p4A plasmid has been placed in several different E. coli strains, including DHI, DH5, BW313, HMS174 and CJ236. In all instances PHB was produced at levels of about 70–95% PHB wt/cell wt.

The p4A plasmid was constructed from pTZ18U-PHB which was constructed from pSB20, which was constructed from pBK12 plasmids containing the PHB biosynthetic pathway. The pBK12 and pSB20 plasmids were disclosed in the copending patent application, Ser. No. 07/362,514, filed Jun. 7, 1989. The p4A plasmid was disclosed in the copending patent application 07/528,549 filed May 25, 1990.

Clone (plasmid) p4A contains the genes for the poly-β-hydroxybutyrate biosynthetic pathway and was deposited in an E. coli HMS174 host in the permanent collection of the American Type Culture Collection, 12301 Parklawn Drive, Rockville, Md., on May 23, 1990 and assigned the accession number ATCC 68329. This deposit is available to the public upon the grant of a patent disclosing it. The deposit is also available as required by foreign patent laws in countries wherein counterparts of the subject application, or its progeny, are filed. However, it should be understood that the availability of a deposit does not constitute a license to practice the subject invention in derogation of patent rights granted by governmental action.

The present invention also advantageously provides that the PHB biosynthetic genes can be obtained from any of the aforementioned plasmids, or subclones thereof, and inserted into an expression vector such as a runaway replication plasmid vector in order to have even greater expression of the PHB polymer. Runaway replication plasmid vectors induce uncontrolled replication (runaway replication) by a simple temperature shift or a change in media constituents, which leads to an increase in plasmid copy number from a few per genome to as much as a thousand or more per genome over a period of only 4–6 cell generations.

Runaway replication plasmid vectors are useful for expressing PHB since PHB has a negative effect on cell growth. When the cell culture is at low density and runaway replication has not been induced, the PHB gene is present in low dosage and expression of PHB is minimized. After high cell density has been reached, runaway replication is induced causing an exponential increase in copy number and gene dosage. The combination of high cell density and rapidly increased gene dosage results in high yield expression of PHB in the relatively short time period before cell growth stops. The PHB biosynthetic genes have been placed into various runaway replication vectors.

A series of new constructs is disclosed herein in which the PHB pathway has been inserted into the runaway replication vectors pRA87, pRA88, pRA89, and pRA90 which were obtained from the Nykomed Pharma Co. of Copenhagen, Denmark. The new constructs are made by inserting the PHB biosynthetic pathway into the plasmids named above. The resulting plasmids are shown in FIGS. 2–6.

Figure 2A:
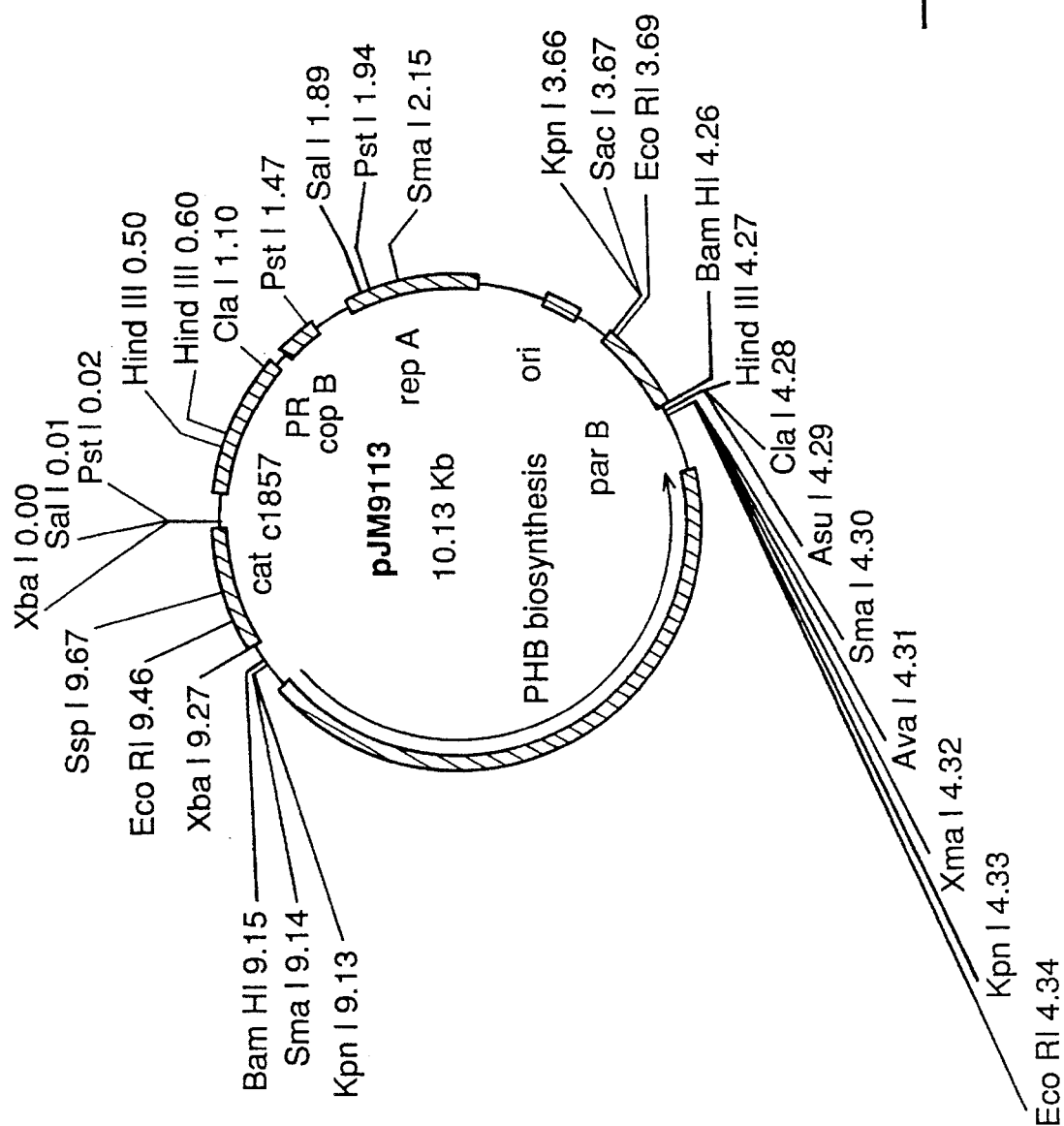
FIGS. 2A and 2B are schematic diagrams of plasmids pJM9113 and pJM9114, respectively.
Figure 2B:
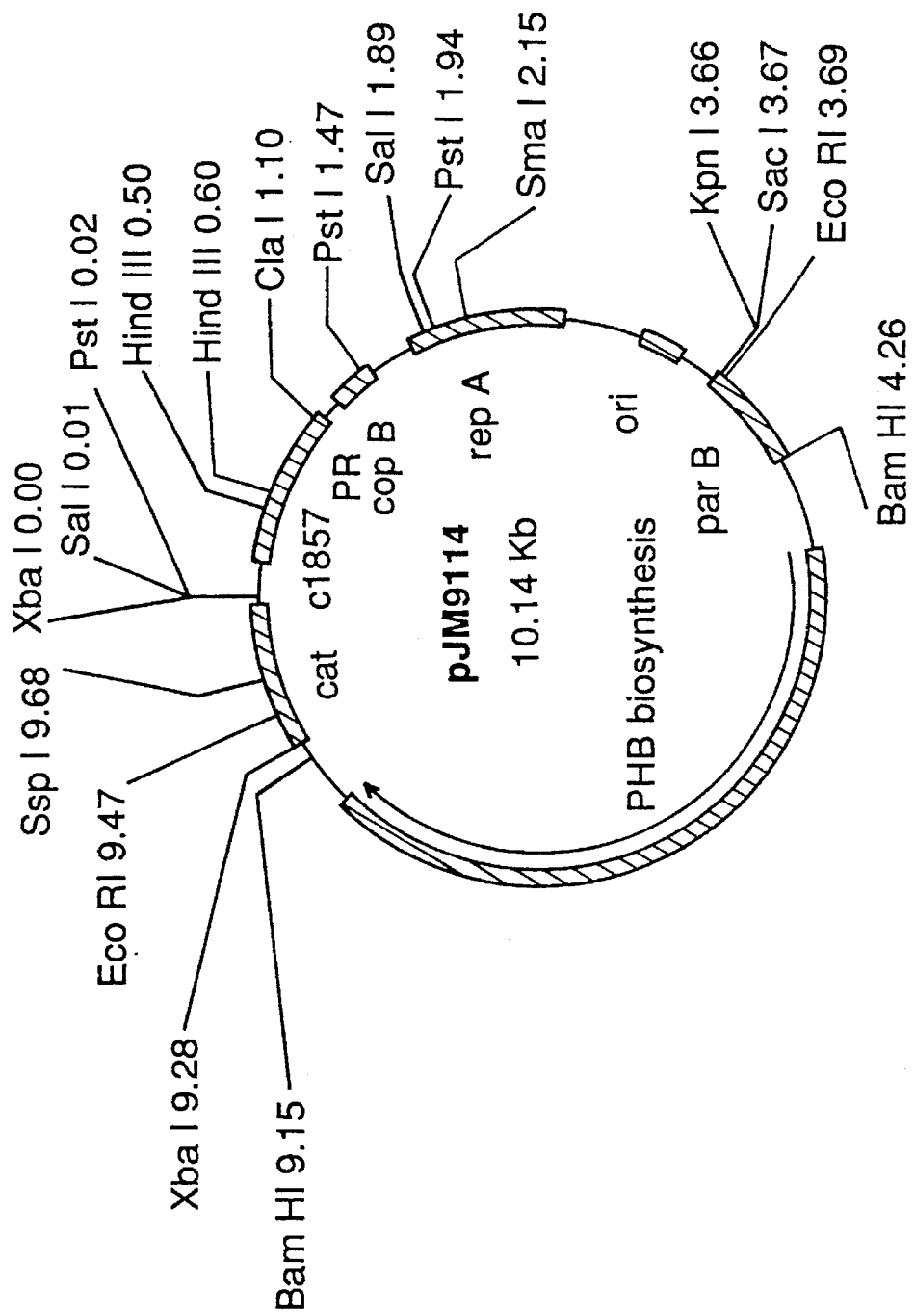

The plasmids pJM9113 and pJM9114, as shown in FIGS. 2A and 2B, respectively, contain the PHB pathway cloned in opposite orientation into the BamHI site of pRA87. The plasmids pJM9113 and pJM9114 are induced into runaway replication above 37° C. and have a basal copy number of 10° at 30° C. Thus, pJM9113 and pJM9114 are both plasmids derived from pRA87, wherein the PHB pathway is in a different orientation in each plasmid.

Figure 3A:
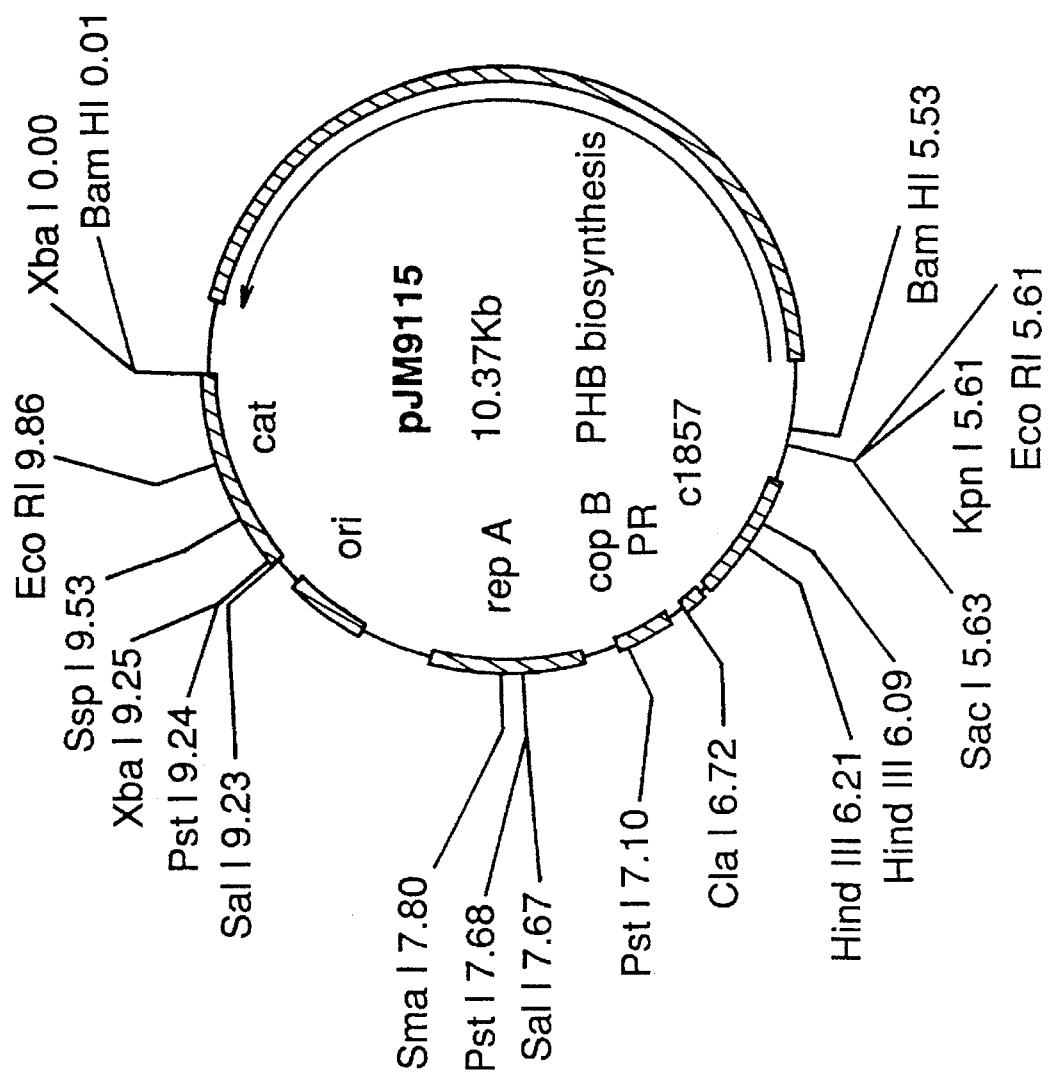
FIGS. 3A and 3B are schematic diagrams of plasmids pJM9115 and pJM9116, respectively.
Figure 3B:
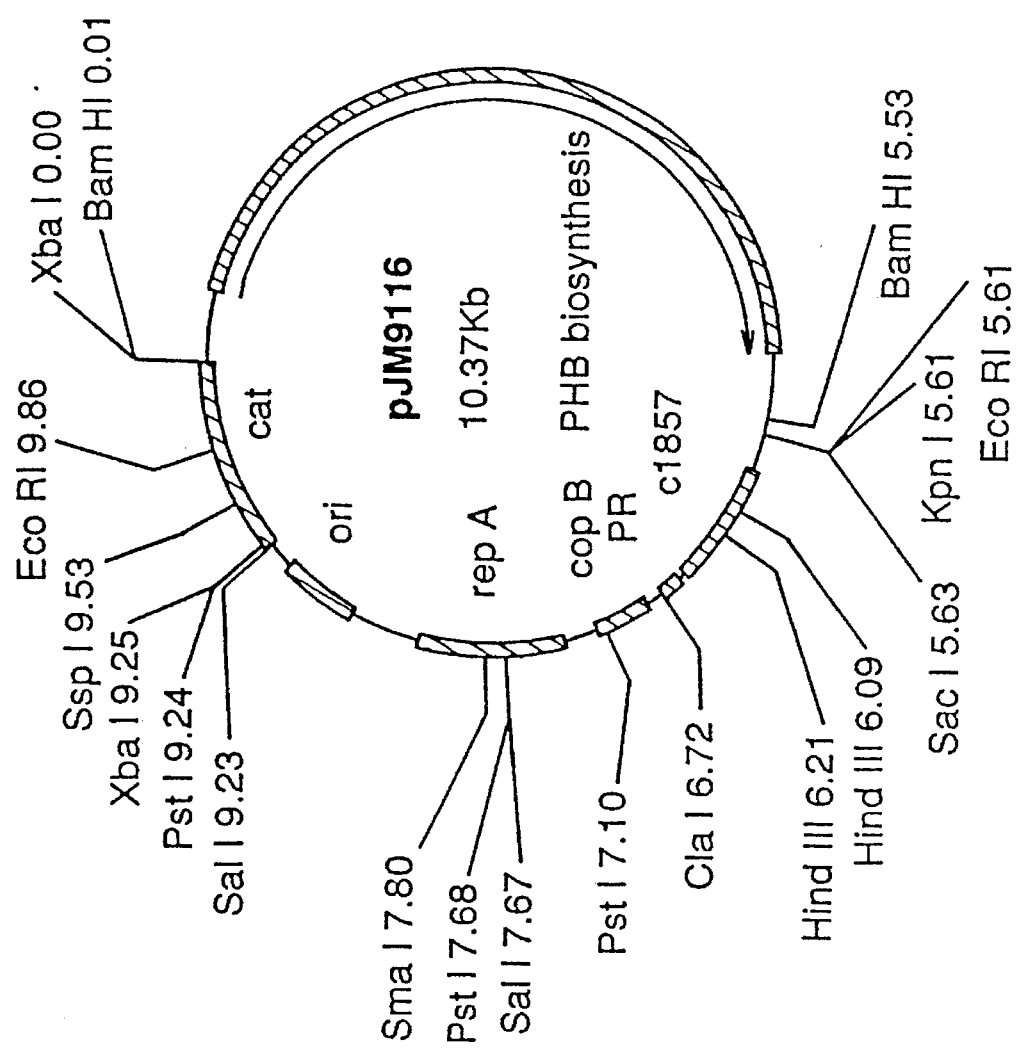

The plasmids pJM9115 and pJM9116, as shown in FIGS. 3A and 3B, respectively, contain the PHB pathway cloned in opposite orientation into the BamHI site of pRA88. The pRA88 plasmid is resistant to chloramphenicol at 30 µg/ml, and has cloning sites BamHI, SacI and KpnI. Thus, pJM9115 and pJM9116 are both plasmids derived from pRA88, wherein the PHB pathway is in a different orientation in each plasmid. The plasmids pJM9115 and pJM9116 are induced into runaway replication at 37° C. and have a basal copy number of 10° at 30° C. When the pJM9116 plasmid is inserted into the E. coli HMS174 host cells, PHB is produced at levels of approximately 85% PHB (by GC analysis) of dry cell weight.

Figure 4A:
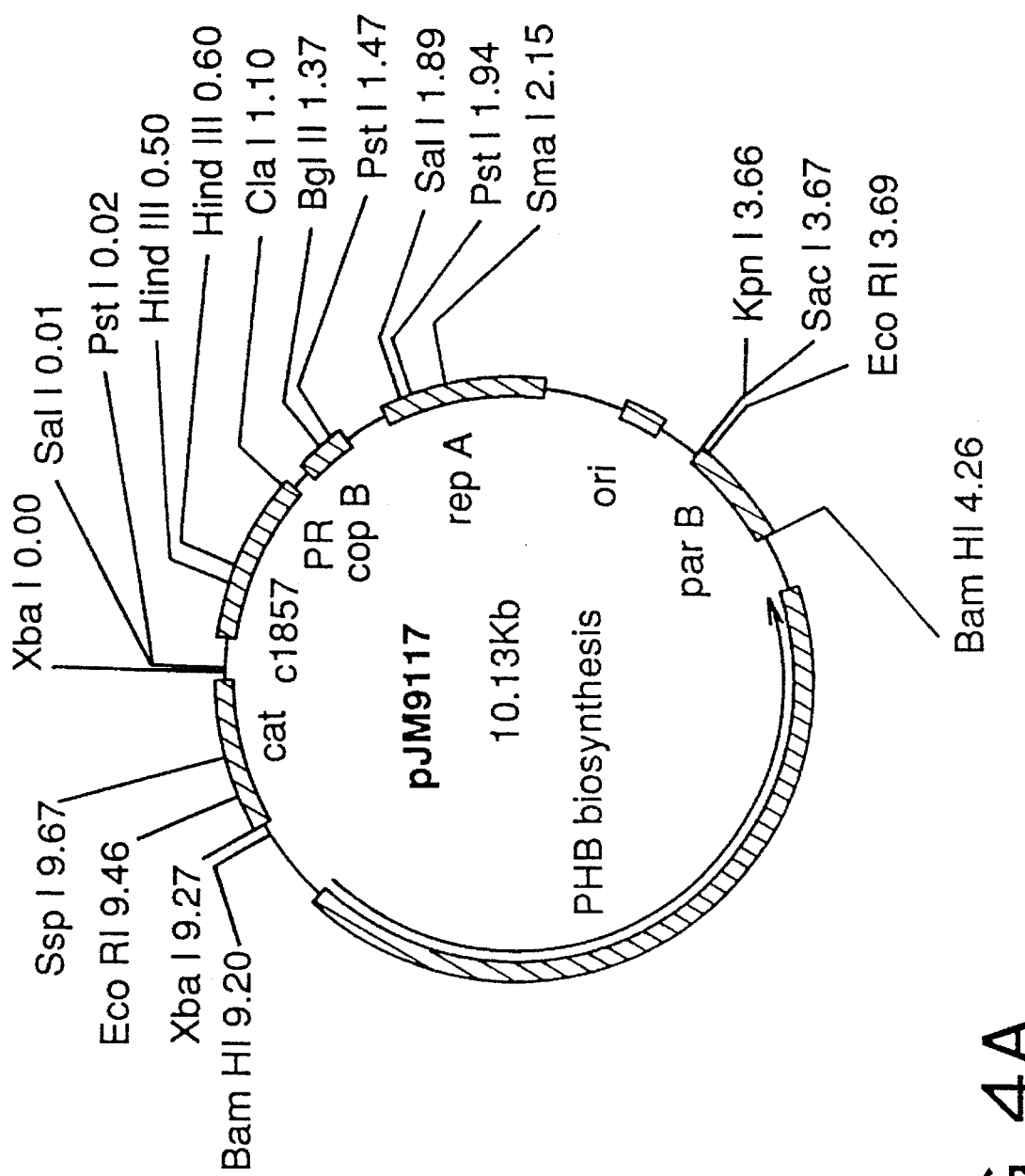
FIGS. 4A and 4B are schematic diagrams of plasmids pJM9117 and pJM9118, respectively.
Figure 4B:
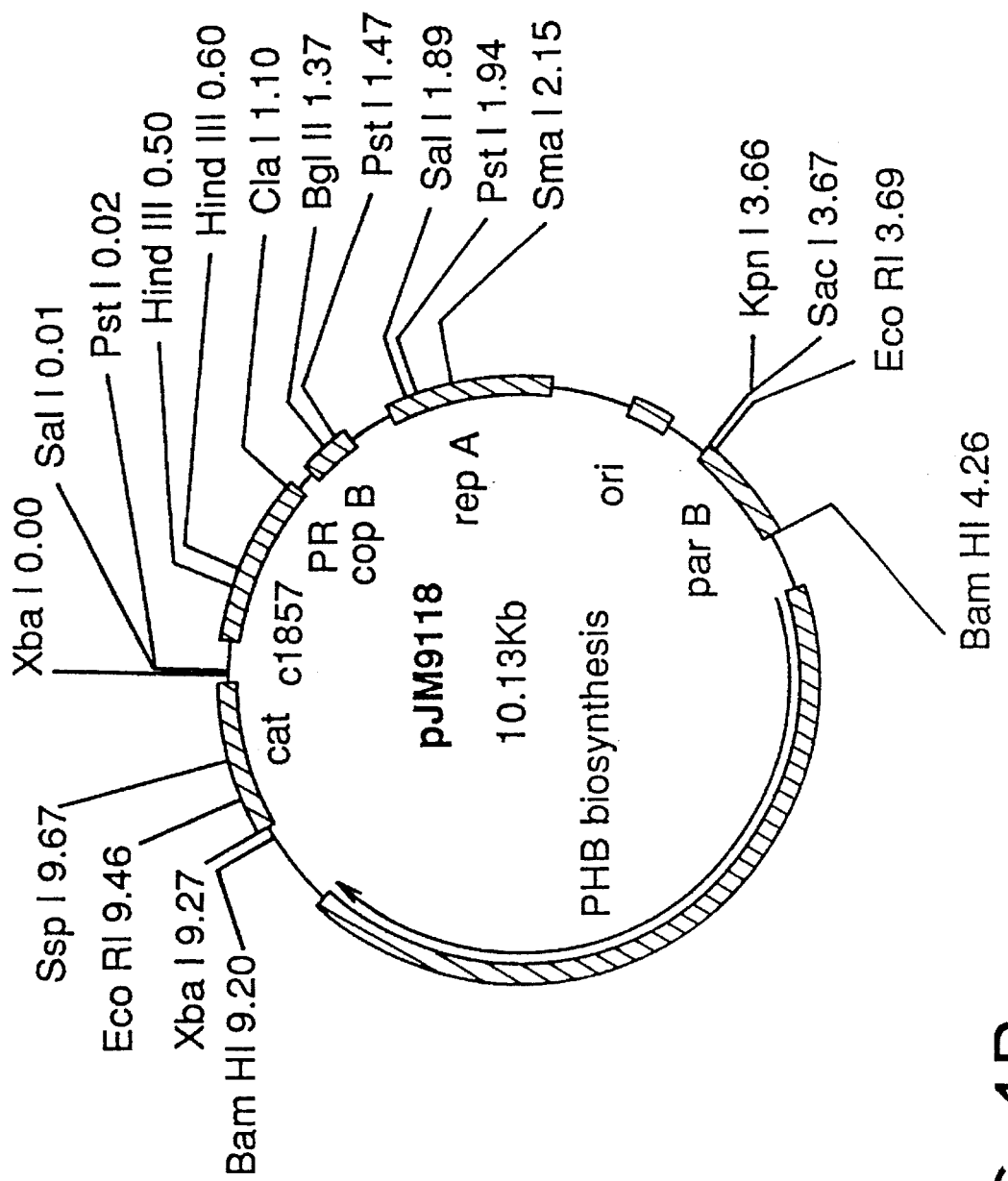

The plasmids pJM9117 and pJM9118, shown in FIGS. 4A and 4B, respectively, contain the PHB pathway cloned in opposite orientation into the BamHI site of pRA89. The plasmid pRA89 cloning sites include Baml, SacI and KpnI. Thus, pJM9117 and pJM9118 are both derived from pRA89 wherein the PHB pathway is in a different orientation in each plasmid. The plasmids pJM9117 and pJM9118 are induced into runaway replication at 41° C. and have a basal copy number of 1.

Figure 5A:
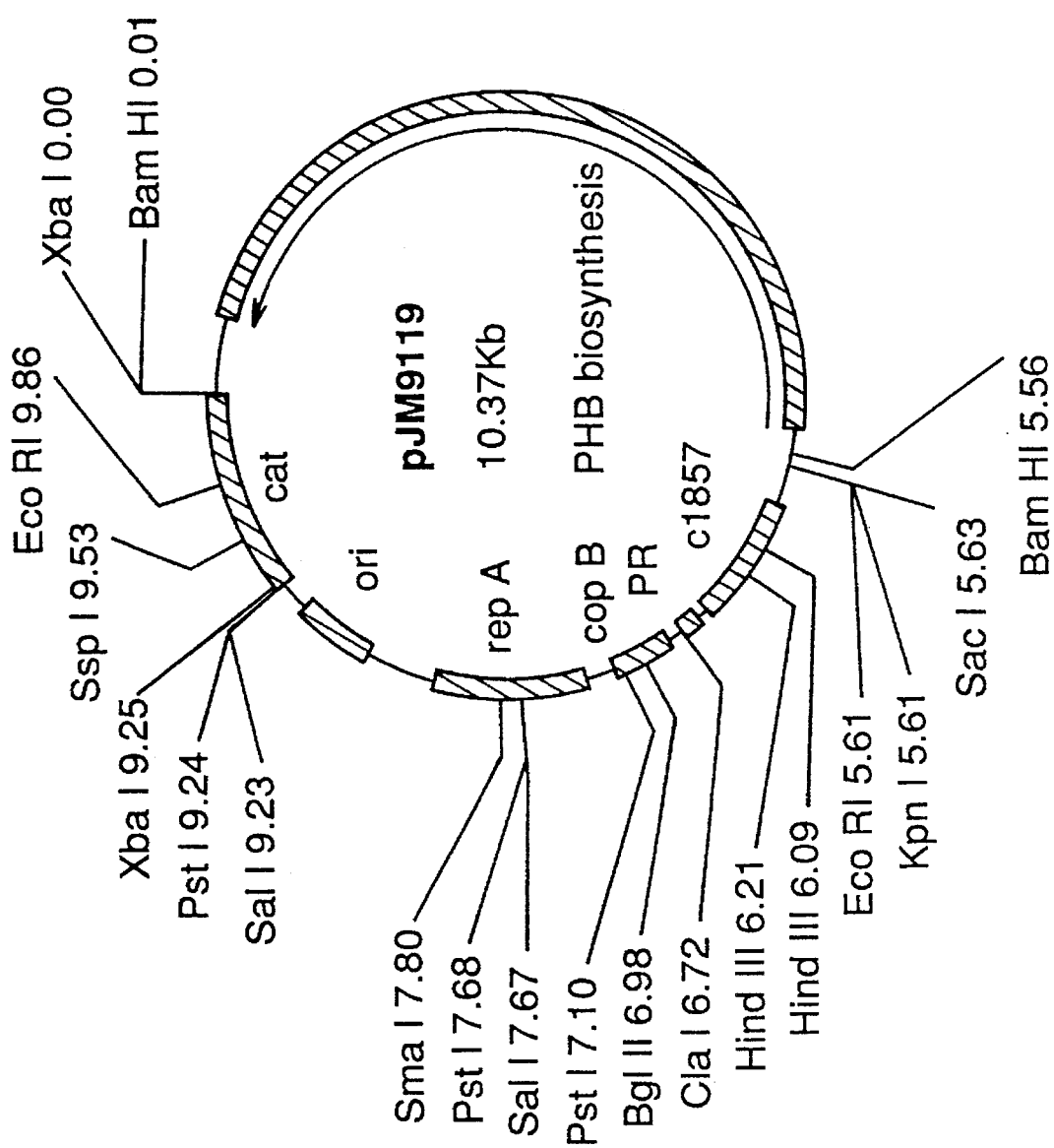
FIGS. 5A and 5B are schematic diagrams of plasmids pJM9119 and pJM9120, respectively.
Figure 5B:
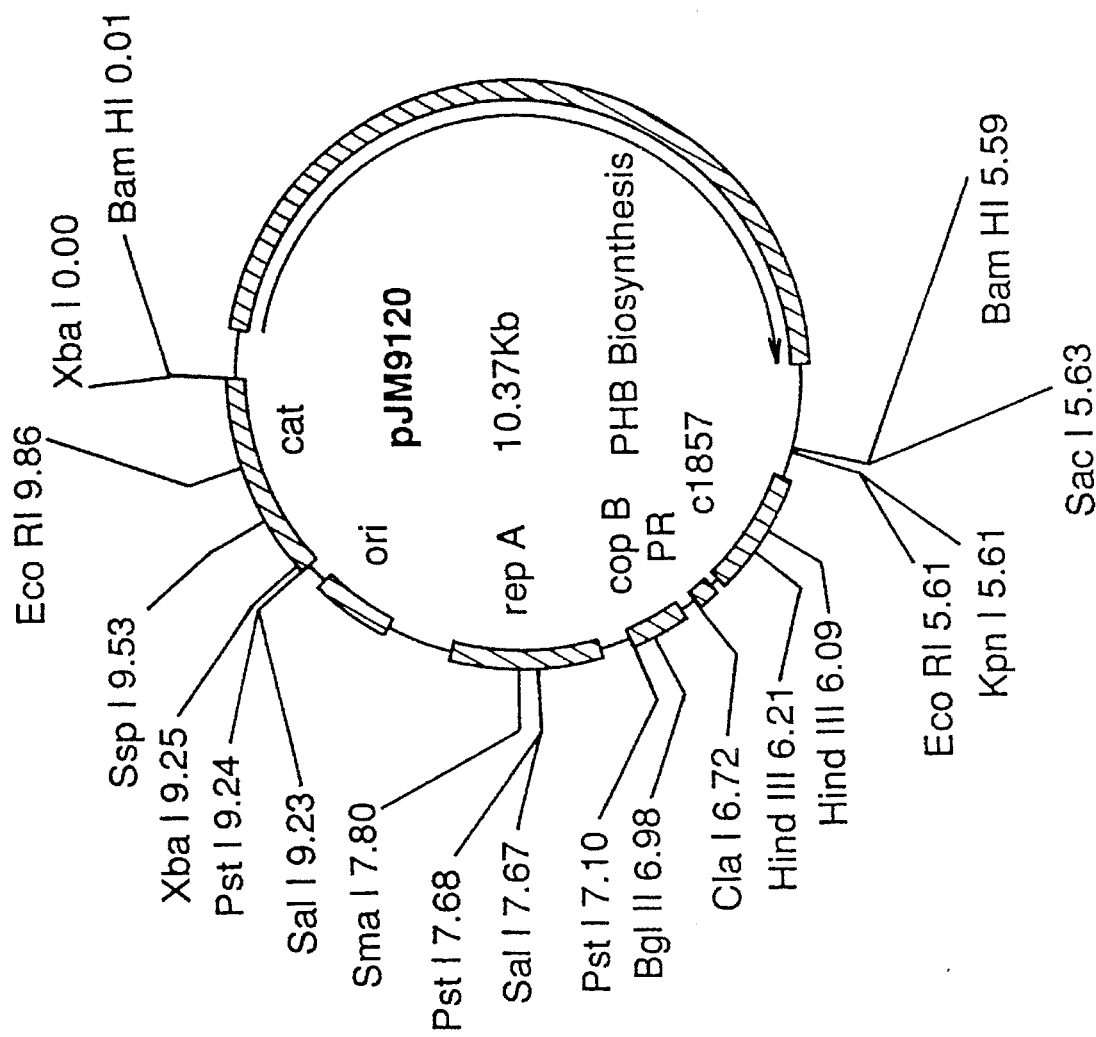

The plasmids pJM9119 and pJM9120, as shown in FIGS. 5A and 5B, respectively, contain the PHB pathway cloned in opposite orientation into the BamHI site of pRA90. The pRA90 is resistant to chloramphenicol at 30 µg/mL and has cloning sites at BamHI, SacI and KpnI. Thus, pJM9119 and pJM9120 are both derived from pRA90 wherein the PHB pathway is in a different orientation in each plasmid.

The plasmids pJM9119 and pJM9120 are induced into runaway replication at 41 ° C. and have a basal copy number of 1.

Figure 6A:
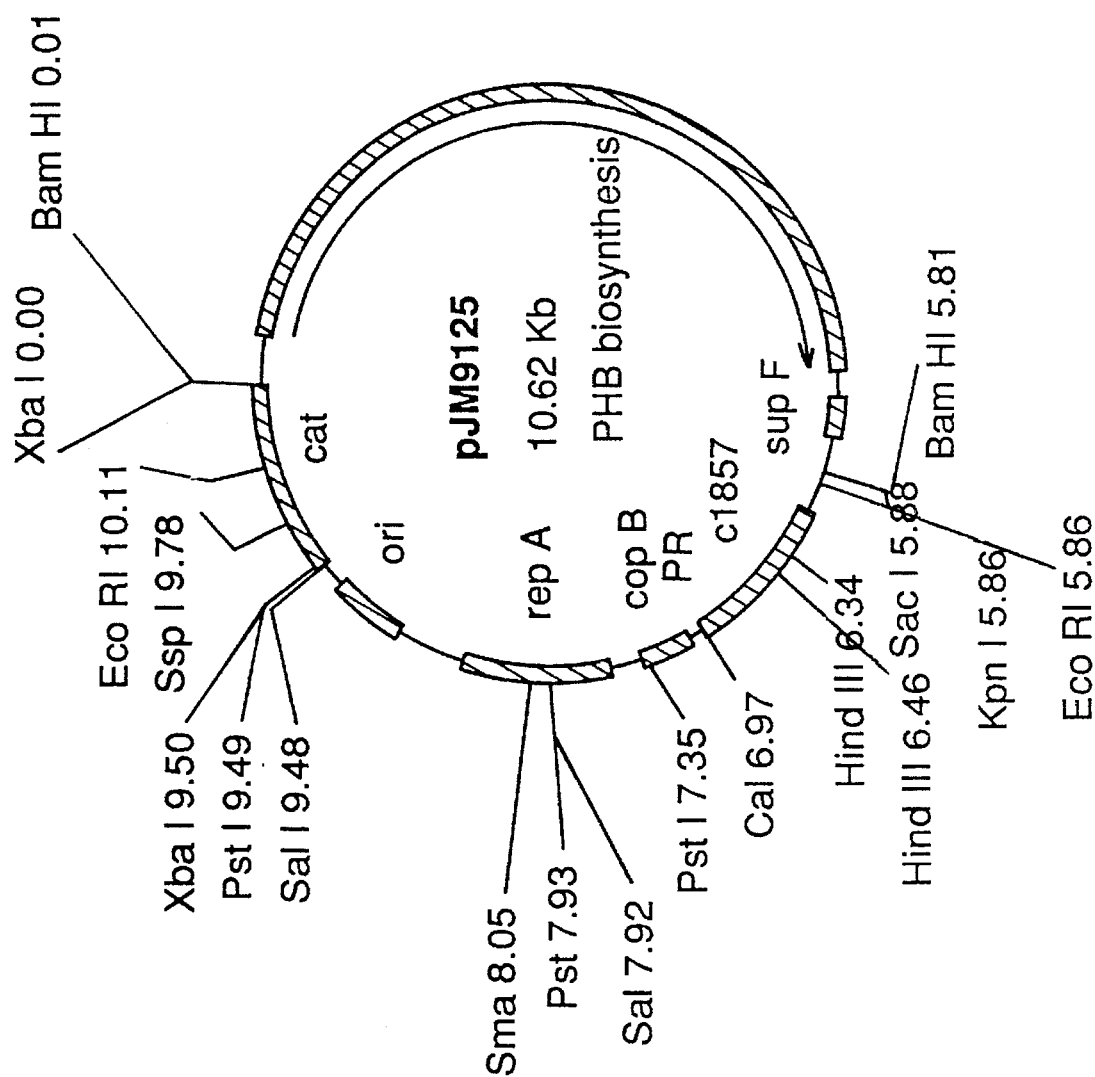
FIGS. 6A and 6B are schematic diagrams of plasmids pJM9125 and pJM9126, respectively.
Figure 6B:
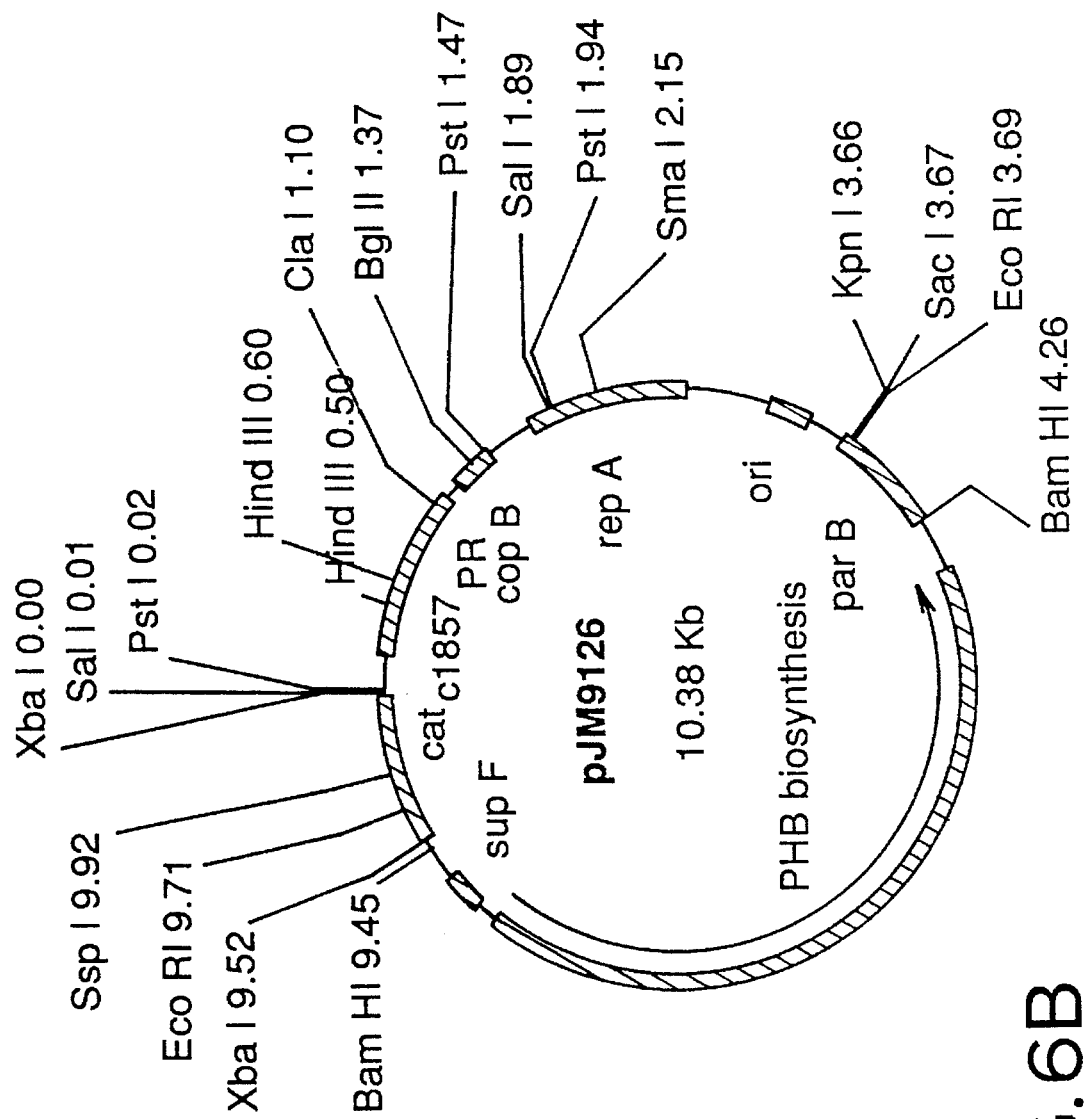

The plasmids pJM9125 and pJM9126, as shown in FIGS. 6A and 6B, respectively, contain the supF gene of E. coli cloned into a BamHI site of the pJM9116 plasmid. The supF gene encodes a transfer RNA that suppresses certain amber mutations and is useful in stabilizing the pJM9125 and pJM9126 plasmids in E. coli cells containing a dnaBam mutation. dnaB codes for the DNA helicase and is absolutely essential for cell growth. In the absence of the suppressor gene (supF) on the plasmid the amber mutation in dnaB would be a lethal mutation, but as long as the plasmid is present, it supplies the necessary suppressor tRNAs to negate the amber mutation in the helicase. On the other hand, if the plasmid is lost, the cell cannot replicate and eventually dies. In the pJM9125 plasmid, the supF gene is cloned into the BamHI site at the end of the PHB pathway. In the pJM9126 plasmid, the supF is cloned into the BamHI site at the end of the PHB pathway in opposite orientation from the pJM9125 plasmid. The plasmids pJM9125 and pJM9126 are induced into runaway replication at 37° C. and have a basal copy number of 10. When the pJM9125 and pJM9126 plasmids are inserted into the E. coli HMS 174 host cells, PHB is produced at levels of approximately 90% PHB (GC analysis) of dry cell weight.

E. coli hosts containing the plasmids of the subject invention were deposited with the American Type Culture Collection (ATCC), 12301 Parklawn Drive, Rockville, Md. 20852, USA. The accession numbers and deposit dates are as follows:

| Culture containing | Accession Nos. | Deposit date |
| --- | --- | --- |
| pJM9101 | ATCC 69000 | May 21, 1992 |
| pJM9113 | ATCC 68989 | May 21, 1992 |
| pJM9114 | ATCC 68990 | May 21, 1992 |
| pJM9115 | ATCC 68991 | May 21, 1992 |
| pJM9116 | ATCC 68992 | May 21, 1992 |
| pJM9117 | ATCC 68993 | May 21, 1992 |
| pJM9118 | ATCC 68994 | May 21, 1992 |
| PJM9119 | ATCC 68995 | May 21, 1992 |
| pJM9120 | ATCC 68996 | May 21, 1992 |
| pJM9125 | ATCC 68998 | May 21, 1992 |
| pJM9126 | ATCC 68999 | May 21, 1992 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122, The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

The present invention also advantageously provides for increased recovery of PHB. To retrieve the purified PHB produced in transformed E. coli in large quantities, the transformed E. coli cells are lysed by genetic means. According to one embodiment, a plasmid containing a lysozyme gene is placed in the E. coli bacterial host cells which contain the PHB biosynthetic pathway on a separate, compatible plasmid. In another embodiment the lysozyme gene is inserted into the plasmid carrying the genes coding for PHB. It is also contemplated that other useful genes, including, for example, a stabilization gene, can also be inserted into the plasmid carrying the PHB coding genes. As the cell grows, more and more lysozyme is made.

Normally, lysozyme cannot cross the inner lipopolysaccharide membrane of the host cell and degrade the middle structural membrane of the cell (peptidoglycan). The lysozyme plasmid causes lysozyme to be continuously made during the growth of the cell. It does not, however, "weaken the cell wall" during the growth period. If it did, the cells could not divide. Instead, the lysozyme is accumulated inside the cell. The inner membrane does not allow the lysozyme to diffuse through to the peptidoglycan layer. As long as the lysozyme is denied access to the peptidoglycan layer by the inner membrane, it does not weaken the cell wall. The presence of the lysozyme plasmid (which is compatible) stabilizes the PHB plasmid and allows more PHB production than normal. At the end of the growth cycle, when the maximum amount of PHB is made, the cells are induced to lysis, for example, in a manner as described in Studier et al. *Methods in Enzymology* 185:60–89 (1990) wherein an agent is added to the cell that permeabilizes (makes holes in) the inner membrane. These agents include, for example, ethylene diamine tetra acetic acid (EDTA). It should be understood that various other permeabilizing agents can be utilized in the present invention.

Once the inner membrane is broken down, the lysozyme starts to weaken the cell wall. Therefore, it is possible to control the time at which the cell wall is weakened. Once the cell wall is weakened, the cells can be lysed by the addition of a suitable nonionic surfactant. One suitable nonionic surfactant comprises Triton® X-100 (octyl phenoxy polyethoxy ethanol) at a concentration ranging from about 0.01% to about 1.0%. A particularly suitable concentration of Triton® X-100 is about 0.1%. It is also contemplated that the cells can be lysed by repeated cycles of freeze-thawing of the cells. The ends of the bacterial cells are destroyed and the PHB granules are extruded out of the ends of the cells. In a preferred embodiment the cells are pelleted by centrifugation, washed, and then resuspended in a permeabilizing agent, such as 50 mM Tris/2 mM EDTA (pH 8) or other suitable agent. The presence of the EDTA allows intracellular lysozyme to weaken the cell wall. A surfactant can be added in a preferred embodiment to a final concentration of 0.1%, to cause almost complete lysis of all the cells thereby releasing the PHB granules.

While the granules of PHB tend to self-aggregate, this aggregation can be enhanced by adding an agglomerating agent. The aggregated PHB granules are then collected. According to the present invention, *E. coli* cells can accumulate PHB to approximately 90–95% of the cell weight, and there is relatively little purification needed after the collection of the PHB, other than washing of the PHB granules.

The various methods employed in the preparation of the plasmids and transformation of host organisms are described in Maniatis, T., Fritsch, E. F., and Sambrook, J. (1982) Molecular Cloning: A Laboratory Manual, Cold Spring Harbor Laboratory, New York.

The restriction enzymes disclosed can be purchased from various commercially available sources. The enzymes are used according to the instructions provided by the supplier.

Two types of assay were used for PHB quantification. In most instances, the procedure of Braunegg et al., *Euro. J. Appl. Microbio. and Biotech.* 6:29 (1978) was used. When necessary to check the data for precision, the procedure of Law et al., *J. Bact.*, 82:33 (1961) was also used.

The following examples are provided to illustrate certain preferred embodiments of the present invention, and are not restrictive of the invention, as claimed.

EXAMPLE 1

The following is an example of electroporation of lysozyme plasmids, pLysS and pLysE, into *E. coli* HMS174(p4A) [Bst B-].

*E. coli* HMS174(p4A) is a strain carrying the p4A plasmid. The restriction enzyme site BstB1, has been deleted from of the plasmid. *E. coli* HMS174 was grown to mid-logarithmetic phase and prepared for electroporation using standard techniques as described in Maniatis, et al. supra. The plasmids pLysS and pLysE, which encode the T7 bacteriophage lysozyme enzyme, were isolated from bacterial strains provided by Brookhaven National Laboratory, Upton, Long Island, N.Y. The pLysS and pLysE plasmids were co-electroporated into the above cells in two separate electroporations. That is, pLysS and p4A (BstB-) were used together, and pLysE and p4A (BstB-) were used together. Electroporated cells were plated into Luria agar plates containing ampicillin, chloramphenicol, and tetracycline. These antibiotics select for the BstB- plasmid, the pLysS and pLysE plasmid, and the HMS174 phenotype, respectively, Four transformants from the pLysS electroporation (designated S1 thru S4) were selected and grown overnight in Luria broth+1% glucose. Five colonies from the pLysE electroporation were selected and also grown as above (designated E1 thru E5). The cultures were grown approximately 24 hours at 37° C. on an orbital shaker incubator. The optical density at 600 nm of each culture was measured, and the relative amount of PHB was measured by dissolving the cellular material with Clorox® (sodium hypochlorite) and reading the resultant optical density of PHB granules at 600 nm. As can be seen in the Table I below the transformants labeled S2, S4 and E5 had very good PHB production.

TABLE I

| Transformants | Optical Density (λ600.0) |
| --- | --- |
| Cells diluted 1:10 | |
| S1 | 1.172 |
| S2 | 1.346 |
| S3 | 1.204 |
| S4 | 1.327 |
| E1 | 0.450 |
| E2 | 0.391 |
| E3 | 0.323 |
| E4 | 0.708 |
| E5 | 1.082 |
| Cells exposed to Clorox ® 1 hr., diluted 1:10 | |
| S1 | 1.096 |
| S2 | 1.145 |
| S3 | 1.037 |
| S4 | 1.208 |
| E1 | 0.163 |
| E2 | 0.088 |
| E3 | 0.044 |
| E4 | 0.352 |
| E5 | 1.013 |

The strain S4, designated as *E. coli* HMS 174(p4A [BstB],pLysS) was deposited in accordance with the terms of the Budapest Treaty with the American Type Culture Collection, 1230 Parklawn Drive, Rockville, Md., under Accession No. 69001, on May 21, 1992. This deposit was made under conditions as provided under ATCC's agreement for Culture Deposit for Patent Purposes, which assures that the deposit will be made available to the U.S. Commissioner of Patents and Trademarks pursuant to 35 USC 122 and 37 CFR 1.114, and will be made available to the public upon issue of a U.S. patent, which requires that the deposit is available to the public upon the grant of a patent disclosing it. The deposit is also available as required by foreign patent laws in countries wherein counterparts of the subject application, or its progeny, are filed. However, it should be understood that the availability of a deposit does not constitute a license to practice the subject invention in derogation of patent rights granted by governmental action.

EXAMPLE 2

The following is an example of lysis of PHB from *E. coli* HMS 174(p4A [BstB-]).

Figure 7A:
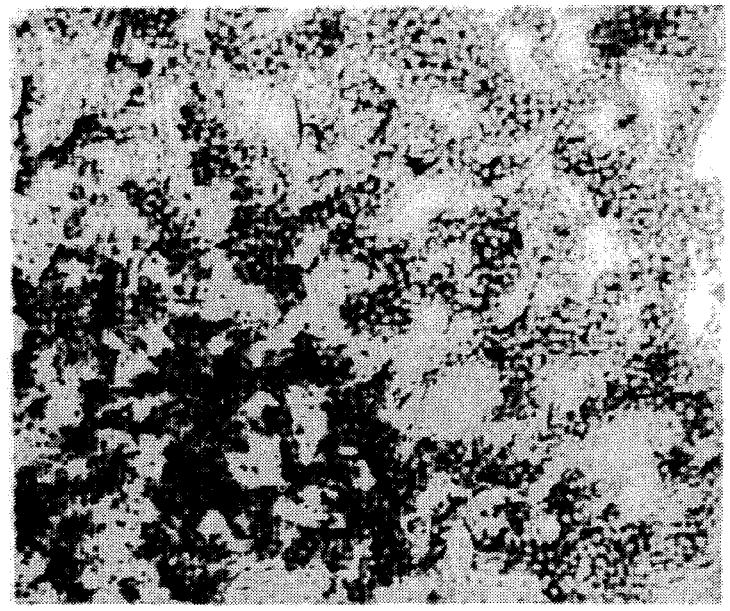
FIGS. 7A and 7B are photographs showing lysis of PHB from clones having the (A) pLysS gene in the S4 strain; and, (B) pLysE gene in the E5 strain.
Figure 7B:
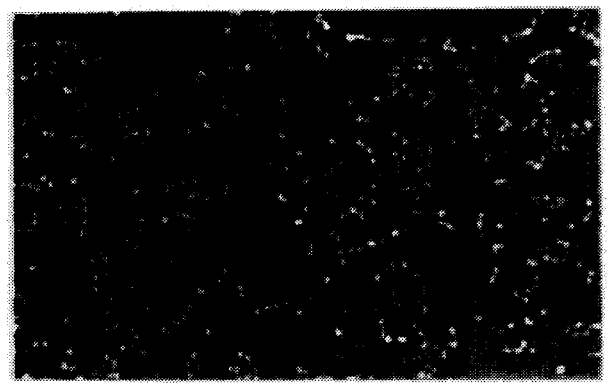

The three transformants in Example 1 above were found to have the greater PHB production (S2, S4 and E5) and were grown in Luria broth containing 1% glucose, 25 µg/ml ampicillin, and 34 µg/ml chloramphenicol for 38 hours at 37° C. (3 ml cultures in 16×100 mm culture tubes). The cells were pelleted by centrifugation, frozen, and then resuspended in 50 mM Tris/2 mM EDTA. Triton® X-100 surfactant was added to 0.1% final concentration. Samples of cells from each strain were placed on microscope slide and examined for lysis. The best clones for lysis were S4 and E5. FIGS. 7A and 7B show these clones after they have accumulated PHB and have been lysed.

EXAMPLE 3

The following is an example of the growth and PHB production the S4 and E5 transformants to determine whether the S4 and E5 lysis strains are as proficient at producing PHB as nonlysis strains.

The three strains which were compared are:

*E. coli* HMS174(p4A)

*E. coli* HMS174(p4A [BstB-], (pLysS) (isolate S4)

*E. coli* HMS174(p4A[BstB-](pLysE) (isolate E5)

Figure 8A:
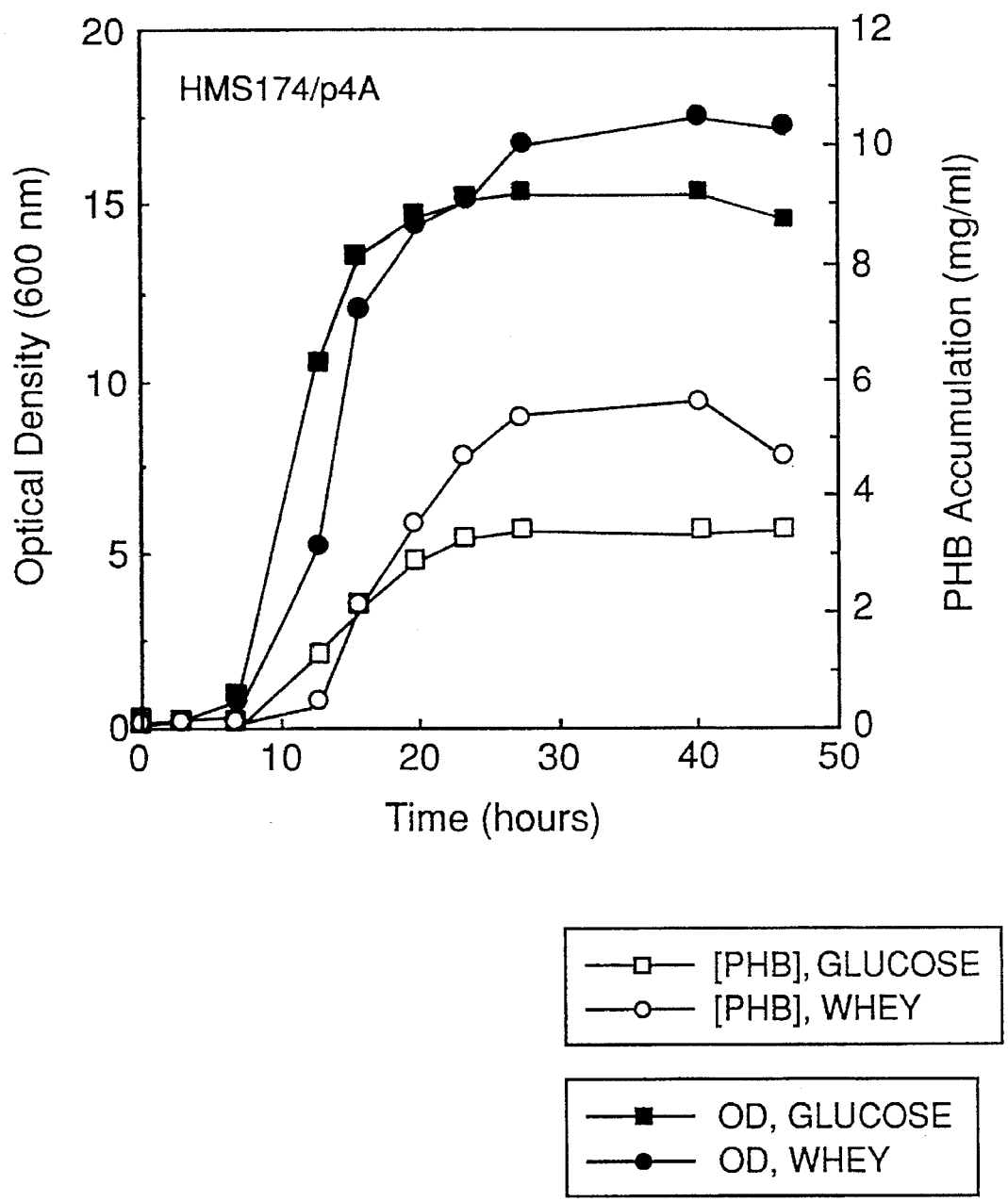
FIGS. 8A, 8B and 8C are graphs showing the growth curves, optical density (600 nm) and PHB accumulation (mg/ml) over time grown on glucose and on whey of (A) strain HMS174/p4A, (B) S4 and (C) E5.
Figure 8B:
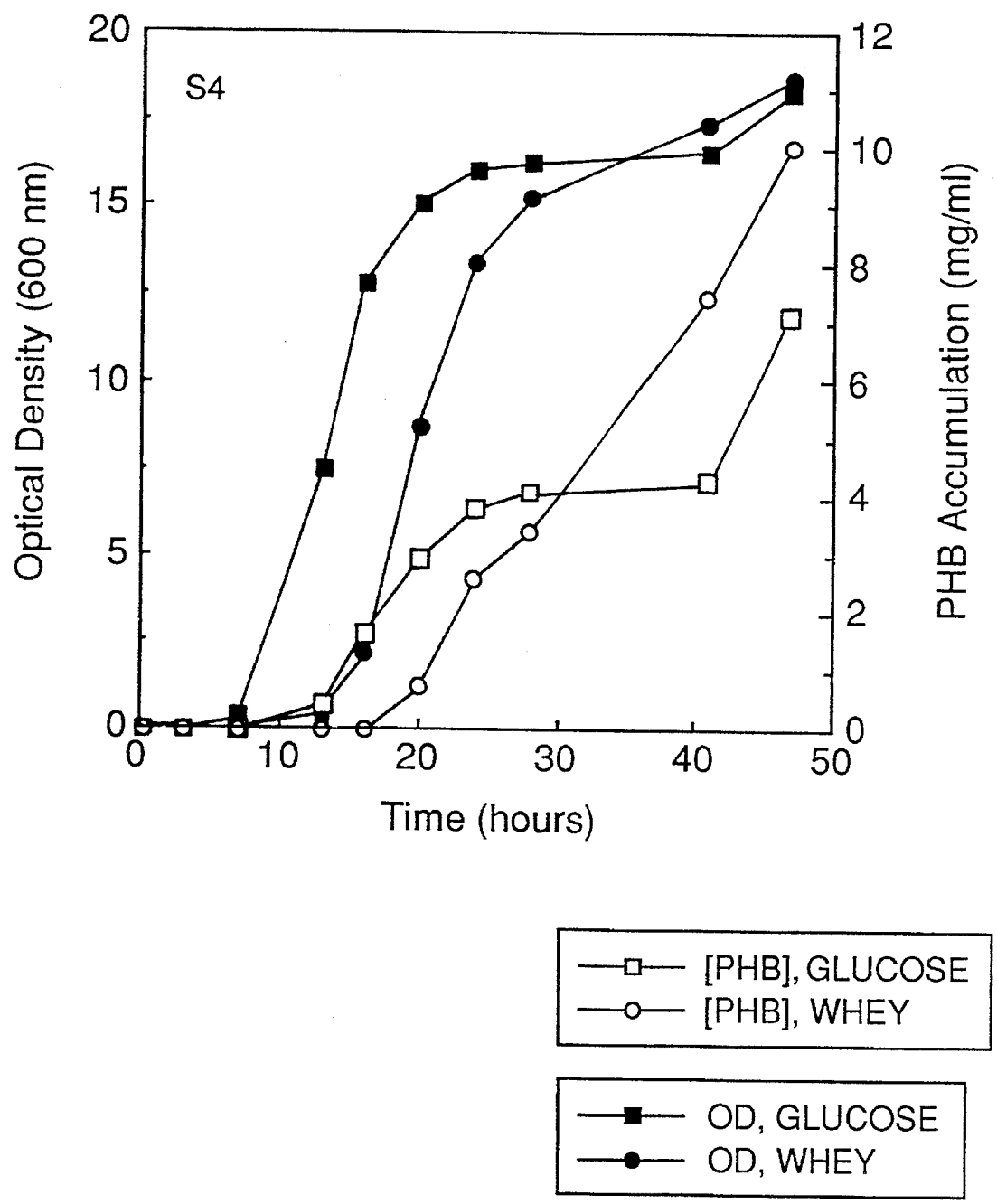
Figure 8C:
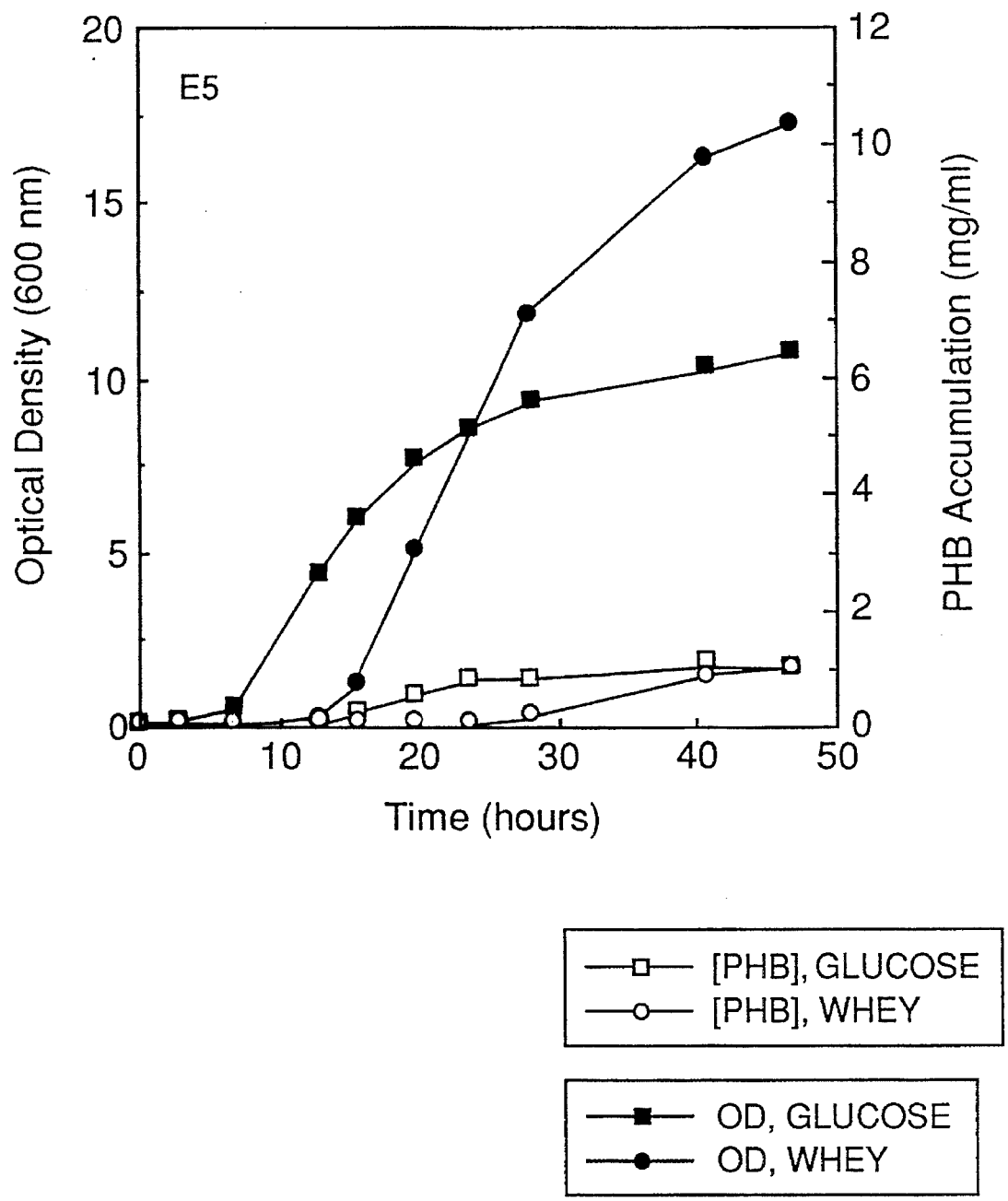

Cultures were grown for approximately 2 days in both glucose and whey (separate cultures). At specified time points, the optical density at 600 nm (rough measure of cell density), and the PHB content (by gas chromatography) was analyzed. PHB production in the lysis strains was compared with PHB producer, *E. coli* HMS 174(p4A). The results shown in FIGS. 8A, 8B and 8C show that the S4 strain (FIG. B) produced PHB as well as the *E. coli* HMS174(p4A) strain (FIG. A).

EXAMPLE 4

Figure 9:
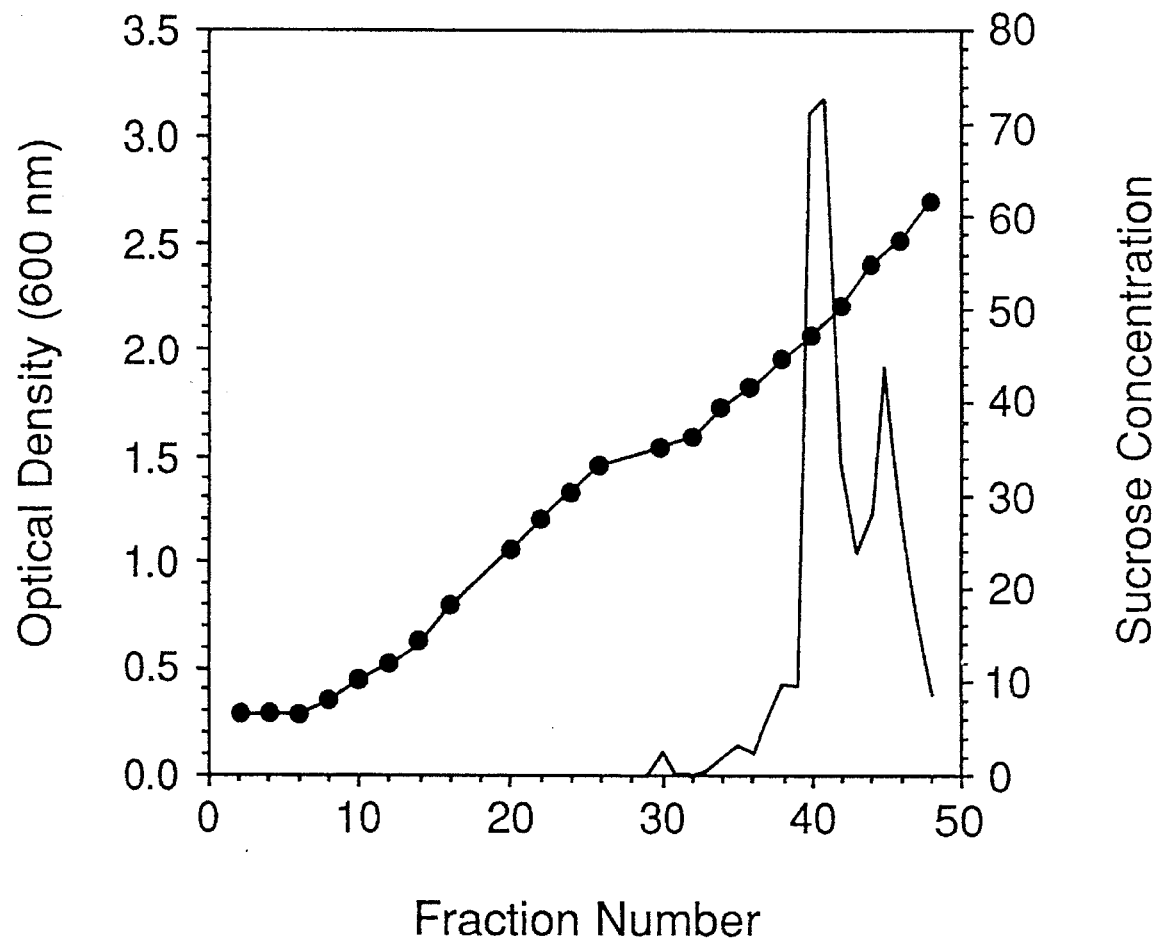
FIG. 9 is a graph showing the isopycnic centrifugation of lysed S4 cells, optical density (600 nm) and sucrose concentration.

The following is an example which shows that PHB granules can be removed from the cell debris after lysis by isopycnic gradient centrifugation. The S4 strain was cultured for 2 days under conditions that promote PHB synthesis. The culture was lysed and loaded onto an isopycnic gradient. The gradient was run for 4 hours at 25,000 rpm at 20° C. The gradient was fractionated and fractions were analyzed for PHB content, optical density at 600 nm, and density. The graph shown in FIG. 9 shows two major peaks, one at fractions 40–41, and the other at fraction 44. These correspond to PHB granule and cell debris, respectively.

EXAMPLE 5

Figure 10:
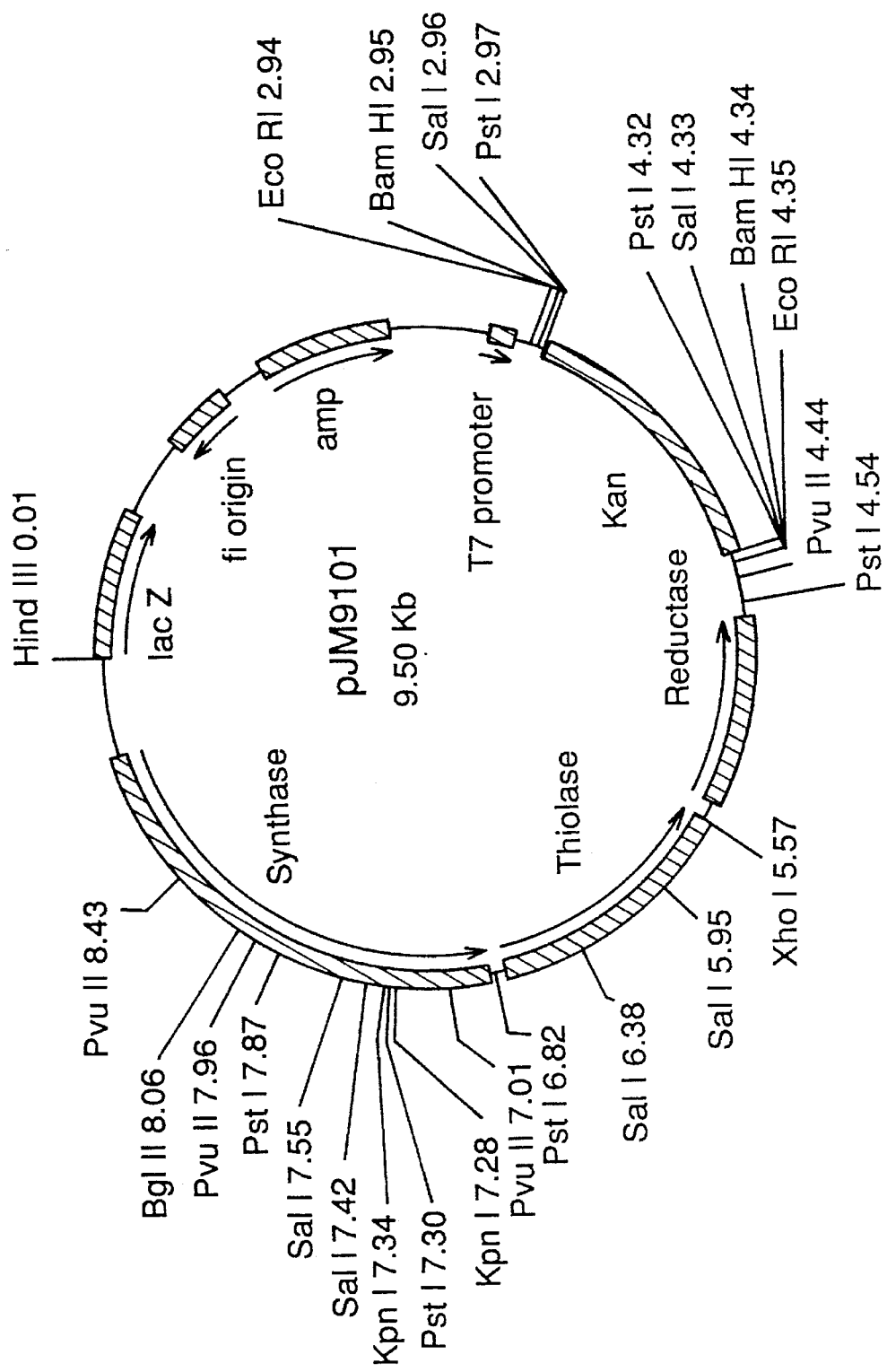
FIG. 10 is a schematic diagram of the plasmid pJM9101.
Figure 11A:
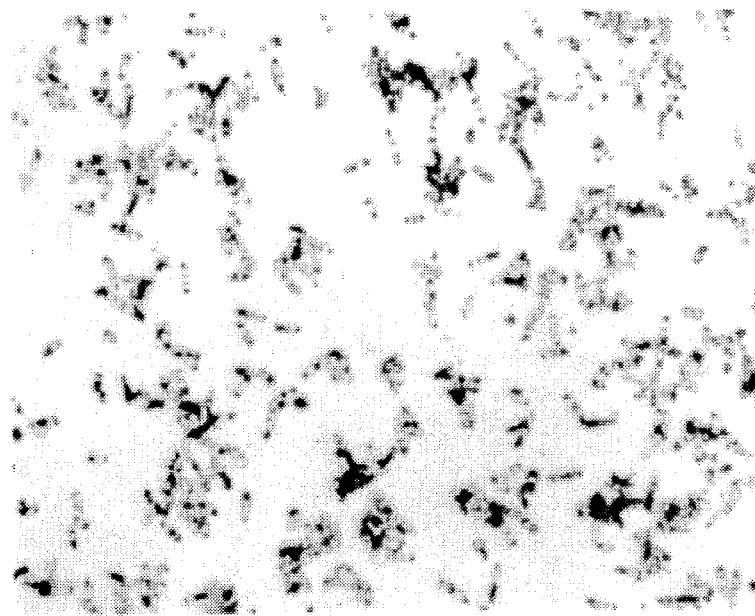
FIGS. 11A and 11B are photographs of (A) PHB production in TRED1.9 cells, and (B) lysis of TRED1.9.
Figure 11B:
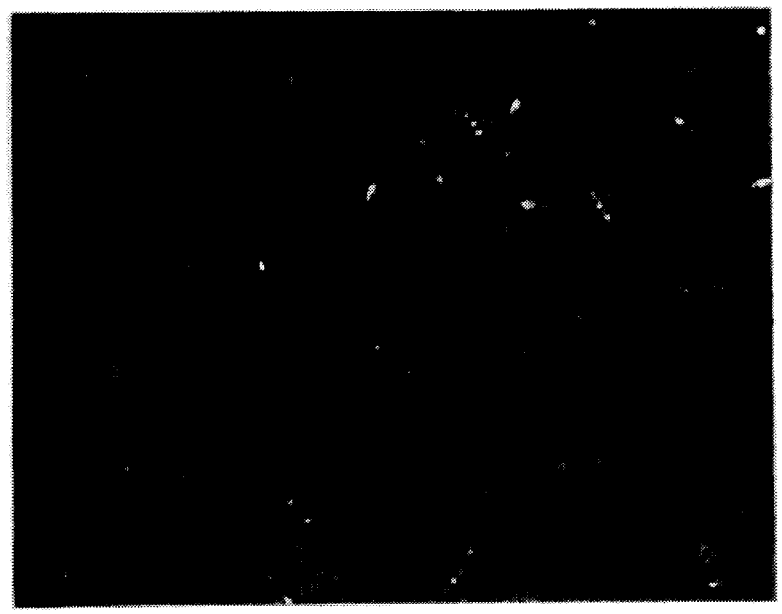

An *E. coli* HMS174 strain (Tred 1.9) was developed which contains the plasmid, pJM9101 as shown in FIG. 10. (The strain Tred 1.9 is the S4 strain in which the p4A plasmid has a kanamycin resistance gene inserted.) The pJM9101 plasmid contains the p4A that has a kanamycin resistance gene inserted at the EcoRI site at the end of the PHB pathway. The strain Tred 1.9 was made by placing pJM9101 and pLysS together in an HMS174 *E. coli*. The strain was tested for lysis proficiency. The strain was grown overnight in 3 ml culture containing kanamycin and chloramphenicol. Cells were harvested by pelleting, resuspended in 50 mM Tris/2 mM EDTA and Triton® X-100 surfactant was added to a final concentration of 0.1%. Lysis, as monitored by light microscopy was nearly 100% complete. Very good PHB production can be seen in the photograph of FIG. 11A. Good lysis and aggregation (arrows) can be seen in the photograph of FIG. 11B.

EXAMPLE 6

Figure 12A:
FIGS. 12A, 12B and 12C are photographs of S4 cells that have been lysed by the disruption of their polar caps.
Figure 12B:
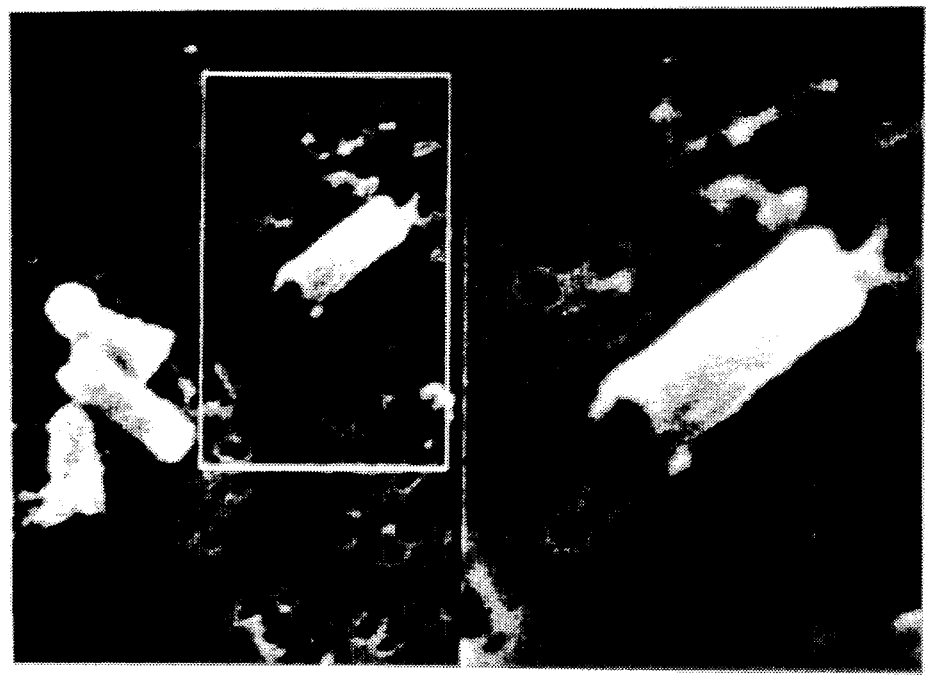
Figure 12C:
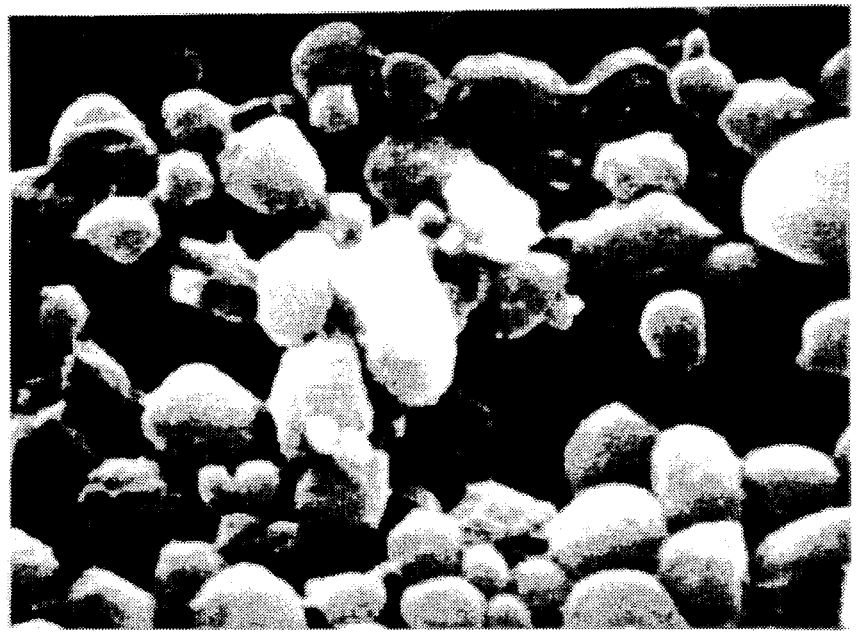

The lysed cells of Example 3 were examined using high magnification microscopy. Standard fixation and electron microscopic techniques were used on 4 cells that had been lysed. The cell lysate mixture was collected on a 0.22 nm membrane filter. The filter was prepared for scanning electron microscopy. The photographs shown in FIGS. 12A, 12B and 12C show aggregated PHB granules that have been released from lysed cells. FIG. 12A shows that the granules are released and tend to self-aggregate. It can also be seen that the cells have been lysed by the disruption of their polar caps. What is left is a small tube with holes at each end. FIG. 12B is a magnification of one of the tubes showing that the polar cap has been "blown off". FIG. 12C is a magnification of the aggregated granules.

EXAMPLE 7

While the granules tend to self-aggregate, the aggregation or agglomeration can be accelerated and controlled by use of an agglomerating agent. Aggregation can be further enhanced by varying the concentration of the agglomerating agent.

Figure 13:
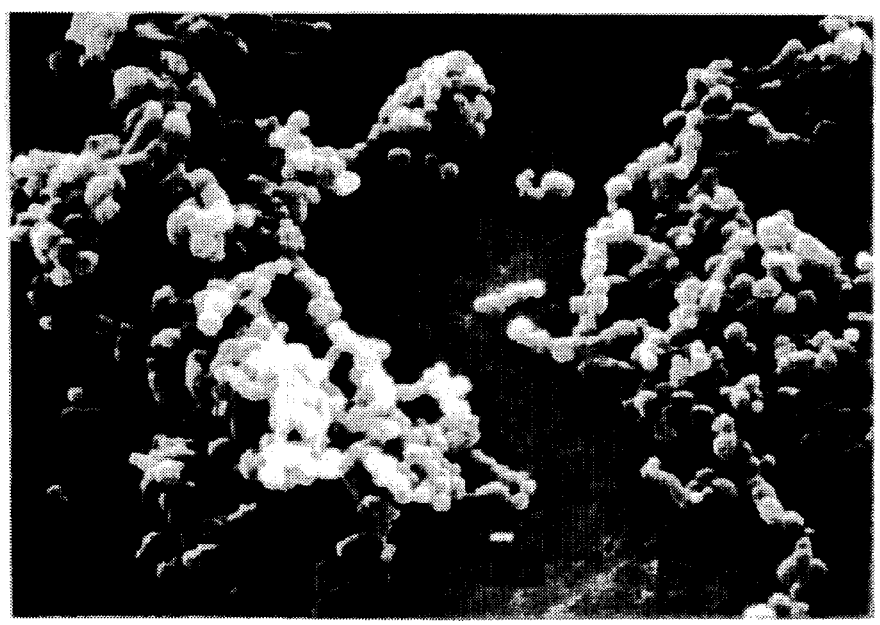
FIG. 13 is a photograph of aggregated granules of PHB.
Figure 14A:
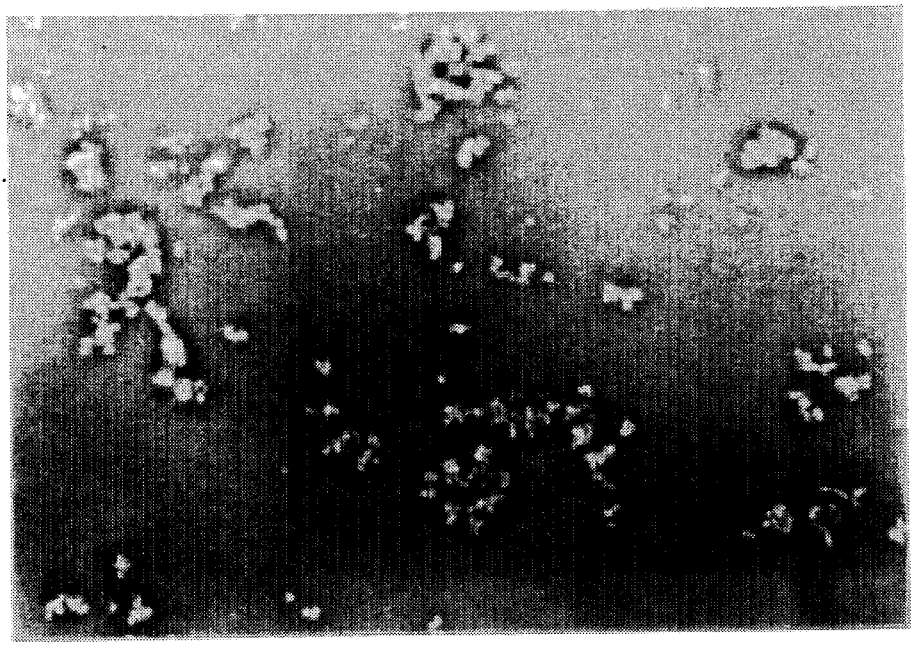
FIG. 14A is a photograph of aggregated granules of PHB.
Figure 14B:
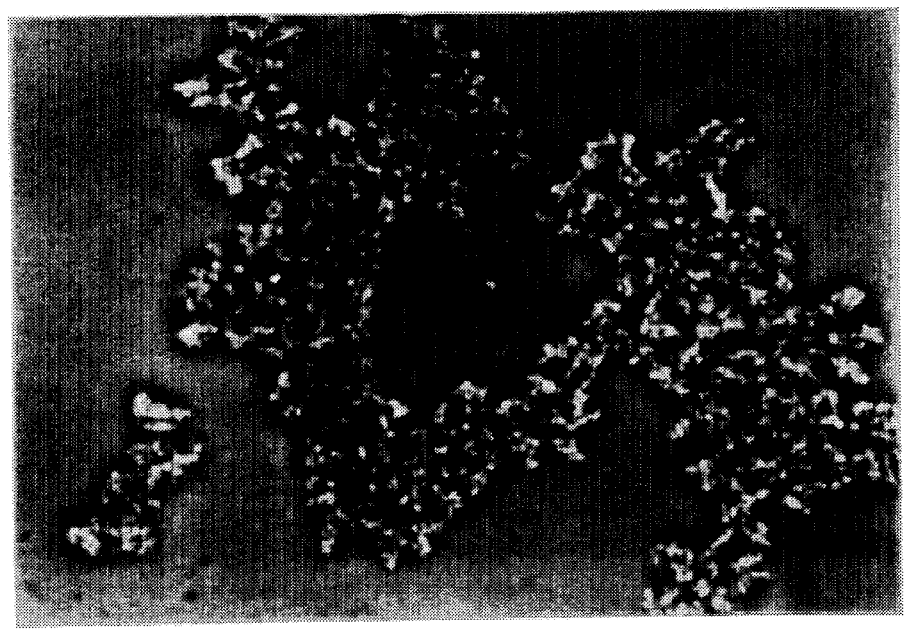
FIG. 14B is a photograph of aggregated granules of PHB using 10 mM calcium chloride as an agglomerating agent.
Figure 14C:
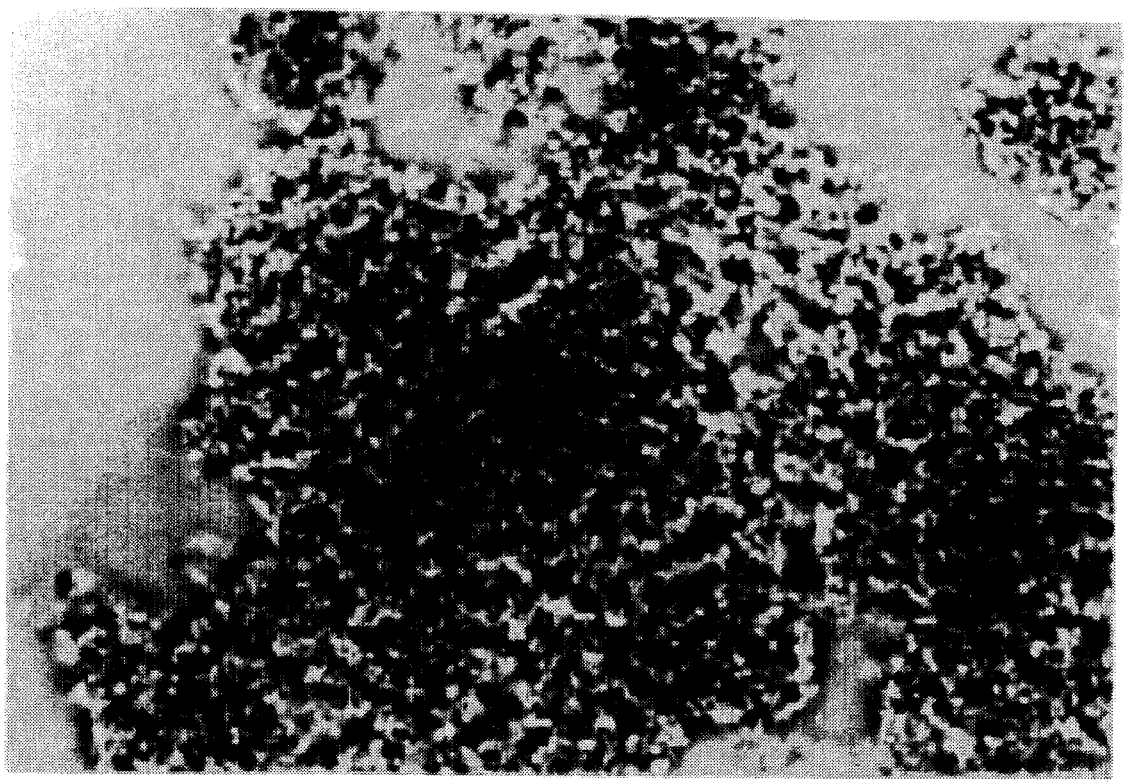
FIG. 14C is a photograph of aggregated granules of PHB using 100 mM calcium chloride as an agglomerating agent.

Suitable agglomeration agents have been disclosed in the application Ser. No. 07/528,549, and include, for example, $KH_2PO_4$ (potassium phosphate-monobasic), NaCl (sodium chloride), $MgSO_4$ (magnesium sulfate), $K_2HPO_4$ (potassium phosphate dibasic), $MgCl_2$ (magnesium chloride), $(NH_4)_2HPO_4$ (ammonium phosphate-dibasic), MgOAC (magnesium acetate), NaOAC (sodium acetate), $CaC_2$ (calcium chloride). FIG. 13 shows a scanning microphotograph of PHB granules aggregated by using calcium chloride. The aggregation of PHB granules is enhanced by increasing the concentration of agglomerating agent. FIG. 14A shows the aggregation of PHB without any agglomerating agent. FIG. 14B shows the aggregation of PHB in the presence of 10 mM calcium chloride as the agglomerating agent. FIG. 14C shows the aggregation of PHB in the presence of 100 mM calcium chloride. It can be seen that the aggregation of PHB is greater using 10 mM calcium chloride and that 100 mM calcium chloride produces even greater aggregation of PHB.

EXAMPLE 8

Figure 15A:
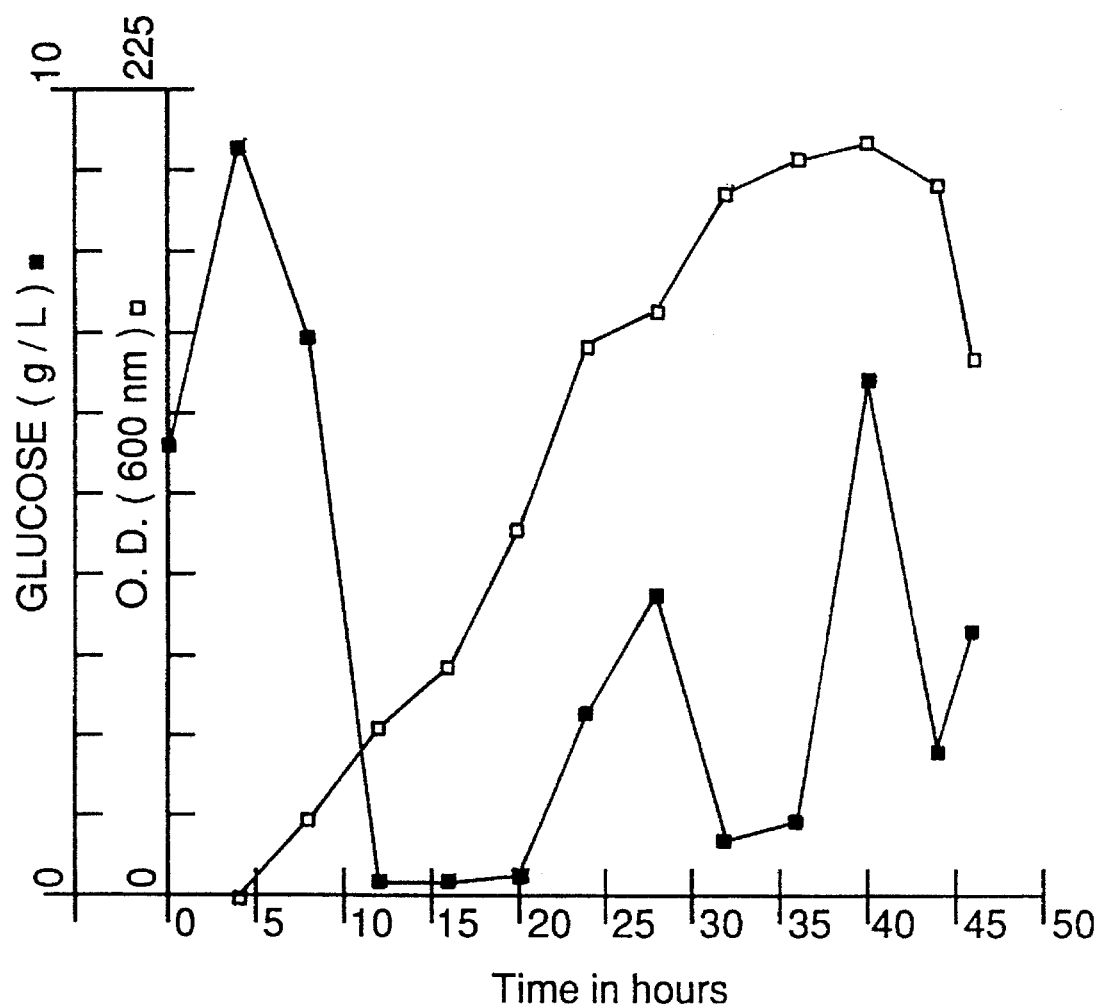
FIG. 15A is a graph showing the optical density O.D. (600nm) of E. coli HMS174 (pJM9125) over time.
Figure 15B:
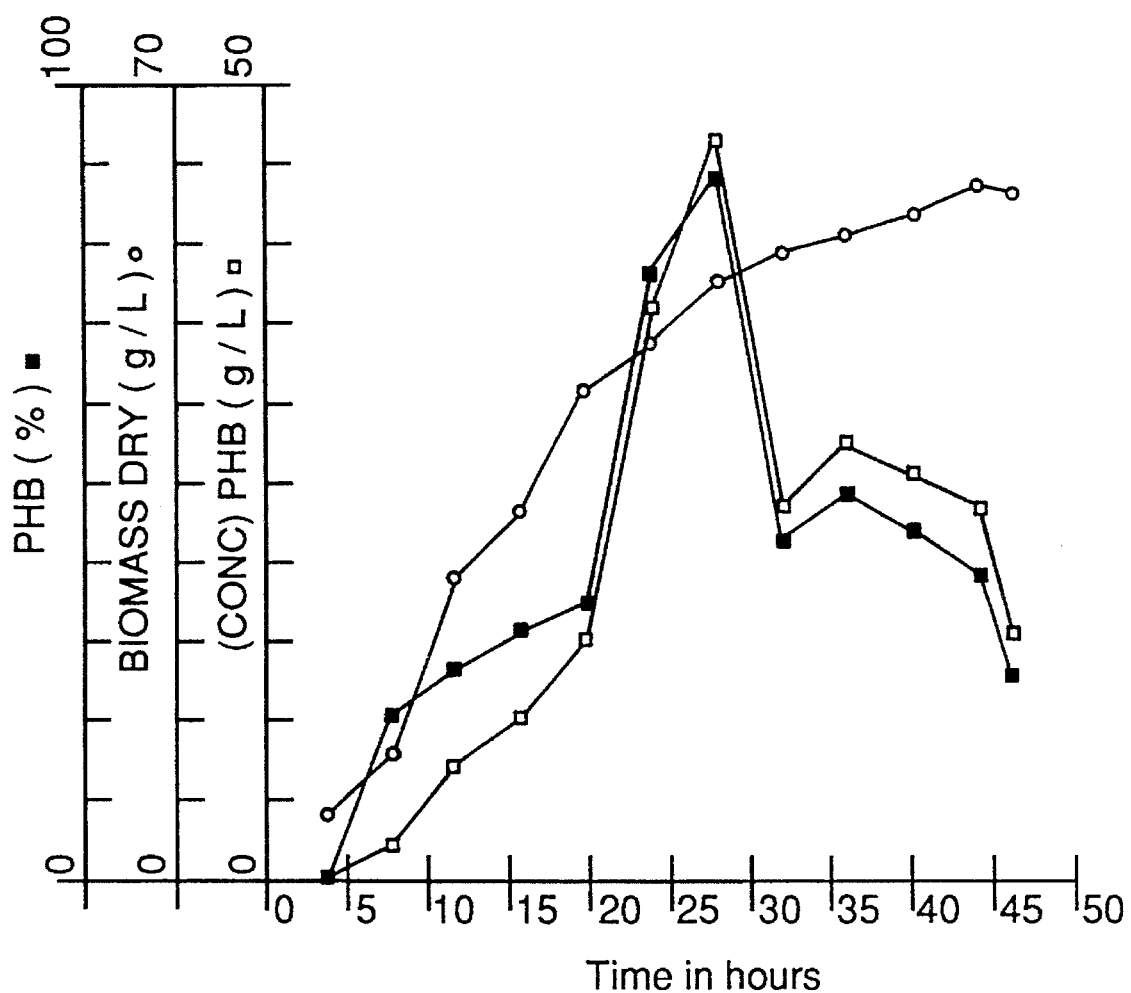
FIG. 15B is a graph of a fermentation experiment showing PHB content (%) ■, dry biomass (conc)(g/L)○, and PHB (conc)(g/L)□.

The following is an example showing the PHB production in an *E. coli* HMS174 containing the plasmid pJM9125. Referring now to FIGS. 15A and 15B, a maximum O.D. of over 200 was attained after 36 hours corresponding to biomass concentrations of up to about 61 g/L. A maximum PHB concentrate of 46.4 g/L was achieved after only 28 hours with a PHB content of 88.2% (corresponding to a total biomass concentration of 52.6 g/L and O.D. of 164). After 28 hours the PHB content dropped sharply. Thus, all the subsequent increase in O.D. and biomass concentration was not associated with PHB production. The PHB yield coefficient at 28 hours was 0.35. The maximum PHB productivity was 1.66 g/L.h The PHB content for the *E. coli* HMS174 (pJM9125) ranged from about 72.6% to about 88.2%.

The descriptions of the foregoing embodiments of the invention have been presented for the purpose of illustration and description. They are not intended to be exhaustive or to limit the invention to the precise forms disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A process for producing poly-β-hydroxybutyrate comprising:

providing a culture of *Escherichia coli* bacterial host cells transformed by (1) a first vector containing a DNA sequence encoding the biosynthetic pathway of poly-β-hydroxybutyrate from *Alcaligenes eutrophus*, wherein the DNA sequence coding for poly-β-hydroxybutyrate comprises thee p4A plasmid, and (2) a second vector containing a DNA sequence of a T7 bacteriophage lysozyme gene;

growing the culture in a suitable medium and obtaining expression of the poly-β--hydroxybutyrate biosynthetic pathway and the lysozyme gene in the *Escherichia coli* bacterial host cells to provide poly-β-hydroxybutyrate and lysozyme;

lysing the *Escherichia coli* bacterial host cells;

isolating the poly-β-hydroxybutyrate; and, collecting the poly-β-hydroxybutyrate.

2. A process for producing poly-β-hydroxybutyrate comprising:

providing a culture of *Escherichia coli* bacterial host cells transformed by (1) a first vector containing a DNA sequence encoding the biosynthetic pathway of poly-β-hydroxybutyrate from *Alcaligenes eutrophus*, wherein the first vector is a plasmid selected from the group consisting of pJM9101, pJM9113, pJM9114, pJM9115, pJM9116, pJM9117, pJM9118, pJM9119, pJM9120, pJM9125, and pJM9126, and (2) a second vector containing a DNA sequence of a T7 bacteriophage lysozyme gene;

growing the culture in a suitable medium and obtaining expression of the poly-β-hydroxybutyrate biosynthetic pathway and the lysozyme gene in the *Escherichia coli* bacterial host cells to provide poly-β-hydroxybutyrate and lysozyme;

lysing the *Escherichia coli* bacterial host cells;

isolating the poly-β-hydroxybutyrate; and, collecting the poly-β-hydroxybutyrate.

3. A process for producing poly-β-hydroxybutyrate comprising:

providing a culture of *Escherichia coli* bacterial host cells, in which the *Escherichia coli* bacterial host cells comprise a strain (S4) designated as *E. coli* HMS174(p4A (BstB-),pLysS), deposited with the American Type Culture Collection under ATCC Accession No. 69001;

growing the culture in a suitable medium and obtaining expression of the poly-β-hydroxybutyrate biosynthetic pathway and the lysozyme gene in the *Escharichia coli* bacterial host cells to provide poly-β-hydroxybutyrate and lysozyme;

lysing the *Escherichia coli* bacterial host cells;

isolating the poly-β-hydroxybutyrate; and, collecting the poly-β-hydroxybutyrate.

4. A process for producing poly-β-hydroxybutyrate comprising:

providing a culture of *Escherichia coli* bacterial host cells transformed by (1) a first vector containing a DNA sequence encoding the biosynthetic pathway of poly-β-hydroxybutyrate from *Alcaligenes eutrophus*, wherein the DNA sequence of the biosynthetic pathway of poly-β-hydroxybutyrate is contained on a high copy number plasmid or on a runaway replication vector, and (2) a second vector containing a DNA sequence of a T7 bacteriophage lysozyme gene;

growing the culture in a suitable medium and obtaining expression of the poly-β-hydroxybutyrate biosynthetic pathway and the lysozyme gene in the *Escherichia coli* bacterial host cells to provide poly-β-hydroxybutyrate and lysozyme;

lysing the *Escherichia coli* bacterial host cells:

isolating the poly-β-hydroxybutyrate; and, collecting the poly-β-hydroxybutyrate at levels of about 90 to about 95%, by weight, of dry cell weight.

5. A process for producing poly-β-hydroxybutyrate comprising:

providing a culture of *Escherichia coli* bacterial host cells transformed by (1) a first vector containing a DNA sequence encoding the biosynthetic pathway of poly-β-hydroxybutyrate from *Alcaligenes eutrophus*, in which the DNA sequence coding for poly-β-hydroxybutyrate is contained on a high copy number plasmid, and (2) a second vector containing a DNA sequence of a T7 bacteriophage lysozyme gene;

growing the culture in a suitable medium and obtaining expression of the poly-β-hydroxybutyrate biosynthetic pathway and the lysozyme gene in the *Escherichia coli* bacterial host cells to provide poly-β-hydroxybutyrate and lysozyme;

lysing the *Escherichia coli* bacterial host cells;

isolating the poly-β-hydroxybutyrate; and, collecting the poly-β-hydroxybutyrate.

6. A process for production of poly-β-hydroxybutyrate, the method comprising transforming an *Escherichia coli* having a dnaβam mutation with a vector containing (1) *Alcaligenes eutrophus* genes coding the biosynthetic pathway of poly-β-hydroxybutyrate and (2) a stabilization gene selected from the group consisting of parB and supF, wherein the genes are expressed by the transformed *Escherichia coli* at sufficient levels to result in the production of poly-β-hydroxybutyrate as a fermentation product when the *Escherichia coli* is grown in an appropriate medium, and wherein said vector is a plasmid selected from the group consisting of, pJM9113, pJM9114, pJM9117, pJM9118, pJM9125 and pJM9126.

7. The method according to claim 6, wherein the *Escherichia coli* has been transformed with pJM9126.

8. The process according to claim 6, wherein the stabilization gene comprises a supF gene.

9. A process for producing poly-β-hydroxybutyrate comprising:

providing a culture of *Escherichia coli* bacterial host cells transformed by (1) a first vector containing a DNA sequence encoding the biosynthetic pathway of poly-β-hydroxybutyrate from *Alcaligenes eutrophus*, wherein the isolated DNA sequence coding for poly-β-hydroxybutyrate is contained on a runway replication vector, and (2) a second vector containing a DNA sequence of a T7 bacteriophage lysozyme gene;

growing the culture in a suitable medium and obtaining expression of the poly-β-hydroxybutyrate biosynthetic pathway and the lysozyme gene in the *Escherichia coli* bacterial host cells to provide poly-β-hydroxybutyrate and lysozyme;

lysing the *Escherichia coli* bacterial host cells;

isolating the poly-β-hydroxybutyrate; and collecting the poly-β-hydroxybutyrate.

10. A process for production of poly-β-hydroxybutyrate, the method comprising transforming an *Escherichia coli* having a dnaBam mutation with a vector containing (1) *Alcaligenes eutrophus* genes coding for the biosynthethic pathway of poly-β-hydroxybutyrate and (2) a stabilization gene selected from the group consisting of parB and supF, wherein the genes are expressed by the transformed *Escherichia coli* at sufficient levels to result in the production of poly-β-hydroxybutyrate as a fermentation product when the *Escherichia coli* is grown in an appropriate medium, and wherein the DNA sequence of the biosynthetic pathway of poly-β-hydroxybutyrate is contained on a runaway replication vector.

11. A process for producing poly-β-hydroxybutyrate comprising:

providing a culture of *Escherichia coli* bacterial host cells tranformed by (1) an isolated DNA sequence coding for the *Alcaligenes eutrophus* biosynthetic pathway of poly-β-hydroxybutyrate, and (2) an isolated DNA sequence of a T7 bacteriophage lysozyme gene;

growing the culture in a suitable medium and obtaining expression of the poly-β-hydroxybutyrate biosynthetic pathway and the lysozyme gene in each *Escherichia coli* bacterial host cell;

isolating the poly-β-hydroxybutyrate by lysing the *Escherichia coli* bacterial host cells; and collecting the poly-β-hydroxybutyrate.

12. The process of claim 11 in which the *Escherichia coli* bacterial host cells are lysed by exposing the cells to a permeabilizing agent of sufficient strength to permeabilize the host cell's inner membrane.

13. The process of claim 12, wherein the host cells are further exposed to a suitable surfactant.

14. The process of claim 11 in which the *Escherichia coli* bacterial host cells are lysed by pelleting the cells and resuspending the cells in a permeabilizing agent.

15. The process of claim 11 in which the *Escherichia coli* bacterial host cells are lysed by pelleting the cells, resuspending the cells in a permeabilizing agent, and thereafter, freezing the cells.

16. The process of claim 11 in which the *Escherichia coli* bacterial host cells comprise *Escherichia coli* HMS 174.

17. The process of claim 11 in which the plasmid is selected from the group consisting of pJM9101, pJM9113, pJM9114, plM9115, plM9116, pJM9117, pMJ9118, pJM9119, pJM9120, pJM9125, and pJM9126.

18. The process of claim 11 in which the *Escherichia coli* bacterial host is transformed by a vector having a DNA sequence coding for poly-β-hydroxybutyrate and a DNA sequence coding for T7 lysozyme.

19. The process of claim 11 in which the isolated DNA sequence of the biosynthetic pathway of poly-β-hydroxybutyrate is contained on a high copy number plasmid.

20. The process of claim 19 in which poly-β-hydroxybutyrate is collected at levels of about 90 to about 95%, by weight, of dry cell weight.

\* \* \* \* \*

UNITED STATES PATENT AND TRADEMARK OFFICE
CERTIFICATE OF CORRECTION

PATENT NO. : 5,512,456
DATED : April 30, 1996
INVENTOR(S) : Douglas E. Dennis

It is certified that error appears in the above-indentified patent and that said Letters Patent is hereby corrected as shown below:

In column 11, claim 1, line 21, please delete "thee" and substitute therefor -- the --.

In column 12, claim 6, line 45, please delete "dnaβam" and substitute therefor
-- dna*Bam* --.

In column 14, claim 17, line 22, please delete "p1M9115, p1M9116" and substitute therefor
-- pJM9115, pJM9116 --.

Signed and Sealed this

Twenty-sixth Day of November 1996

Attest:

BRUCE LEHMAN

Attesting Officer          Commissioner of Patents and Trademarks